United States Patent
Sano et al.

(10) Patent No.: US 7,603,182 B2
(45) Date of Patent: Oct. 13, 2009

(54) ULTRASONOGRAPH, WORK FLOW EDITION SYSTEM, AND ULTRASONOGRAPH CONTROL METHOD

(75) Inventors: Akihiro Sano, Tochigi (JP); Naohisa Kamiyama, Tochigi (JP); Yoichi Ogasawara, Tochigi (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 552 days.

(21) Appl. No.: 10/494,683

(22) PCT Filed: Nov. 22, 2001

(86) PCT No.: PCT/JP01/10235

§ 371 (c)(1),
(2), (4) Date: May 5, 2004

(87) PCT Pub. No.: WO03/043501

PCT Pub. Date: May 30, 2003

(65) Prior Publication Data

US 2004/0254465 A1    Dec. 16, 2004

(51) Int. Cl.
*G05B 11/01* (2006.01)
(52) U.S. Cl. .................... 700/15; 382/128; 600/437
(58) Field of Classification Search .............. 382/128; 700/15
See application file for complete search history.

(56) References Cited

U.S. PATENT DOCUMENTS

| | | | | |
|---|---|---|---|---|
| 5,619,995 A | * | 4/1997 | Lobodzinski | 600/425 |
| 5,950,002 A | * | 9/1999 | Hoford et al. | 717/109 |
| 6,014,581 A | * | 1/2000 | Whayne et al. | 600/523 |
| 6,306,089 B1 | * | 10/2001 | Coleman et al. | 600/437 |
| 6,458,081 B1 | * | 10/2002 | Matsui et al. | 600/437 |
| 6,540,676 B2 | * | 4/2003 | Kamiyama | 600/437 |
| 6,707,469 B1 | * | 3/2004 | Kelly | 715/744 |
| 6,904,161 B1 | * | 6/2005 | Becker et al. | 382/128 |
| 6,953,433 B2 | * | 10/2005 | Kerby et al. | 600/443 |
| 2002/0193676 A1 | * | 12/2002 | Bodicker et al. | 600/407 |
| 2002/0196376 A1 | * | 12/2002 | Symoen et al. | 348/734 |
| 2002/0198454 A1 | * | 12/2002 | Seward et al. | 600/437 |
| 2003/0013951 A1 | * | 1/2003 | Stefanescu et al. | 600/407 |

FOREIGN PATENT DOCUMENTS

JP        3-206556        9/1991

(Continued)

*Primary Examiner*—Brian Casler
*Assistant Examiner*—Parikha S Mehta
(74) *Attorney, Agent, or Firm*—Oblon, Spivak, McClelland, Maier & Neustadt, L.L.P.

(57) ABSTRACT

The present invention relates to an ultrasonic diagnostic equipment 1 which projects ultrasonic signals into a patient, and which generates an ultrasonic image on the basis of reflection echoes from within the patient. The ultrasonic diagnostic equipment 1 comprises a workflow system 21 which controls equipment operations including the generation of the ultrasonic image, in accordance with a workflow protocol based on the examination procedure of steps created beforehand, and a visual workflow editor 22 which is so constructed as to edit the workflow protocol visually with icons on a screen. Owing to the configuration, the creation of the workflow protocol is facilitated, chances for the utilization of the workflow system are expanded, and even users, such as beginners, who are slightly skilled in the ultrasonic diagnostic equipment and have experienced operations little, are permitted to master the operating method of the equipment promptly and to operate the equipment more easily.

4 Claims, 28 Drawing Sheets

FOREIGN PATENT DOCUMENTS

| | | |
|---|---|---|
| JP | 4-506162 | 10/1992 |
| JP | 6-30910 | 2/1994 |
| JP | 6-110673 | 4/1994 |
| JP | 08-182680 | 7/1996 |
| JP | 9-258971 | 10/1997 |
| JP | 10-216126 | 8/1998 |
| JP | 10-232767 | 9/1998 |
| JP | 2001-137237 | 5/2001 |
| JP | 2001-147704 | 5/2001 |

* cited by examiner

| SORTS OF TOOL BUTTONS | FUNCTIONS |
|---|---|
| TB1 | CREATE WORKFLOW DESIGN SCREEN ANEW |
| TB2 | LOAD WORKFLOW DATA SAVED IN LOCAL DISK |
| TB3 | SAVE WORKFLOW DATA IN LOCAL DISK |
| TB4 | EXPORT DATA IN ORDER TO UTILIZE WORKFLOW DATA IN VISUAL EDITOR ON OTHER ULTRASONIC DIAGNOSTIC EQUIPMENT OR EXTERNAL PC |
| TB5 | CREATE SUBWORKFLOW |
| TB6 | ENTER COMMENTS |
| TB7 | DELETE SELECTED OBJECT |
| TB8 | DISPLAY HELP |

(NO GOOD)

(GOOD)

FIG. 32

| PROPERTY | DESCRIPTION |
| --- | --- |
| AUTOMATIC EXECUTION | ACTIVITY IS AUTOMATICALLY EXECUTED WITHOUT WAITING USER ACTION IN WORKFLOW SYSTEM OPERATION |
| MANUAL EXECUTION | USER ACTION IS WAITED IN WORKFLOW SYSTEM OPERATION, AND ACTIVITY IS EXECUTED UPON ACTION |
| SKIP | ACTIVITY IS NOT EXECUTED IN WORKFLOW SYSTEM OPERATION. PAS EXECUTES NEXT ACTIVITY |
| CONDITIONAL EXECUTION | ACTIVITY CAN BE EXECUTED, OR SKIPPED OR JUMPED IN ACCORDANCE WITH EXECUTION STATUS WHICH ACTIVITY REPLIES IN WORKFLOW SYSTEM OPERATION |

FIG. 33

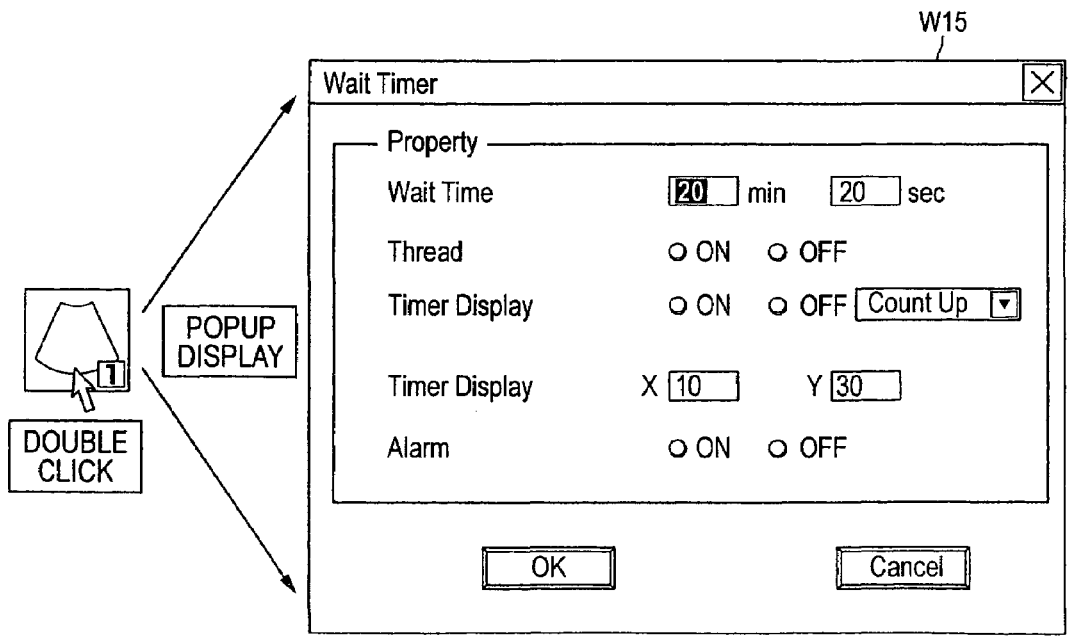

ULTRASONOGRAPH, WORK FLOW EDITION SYSTEM, AND ULTRASONOGRAPH CONTROL METHOD

TECHNICAL FIELD

The present invention relates to an ultrasonic diagnostic equipment which depicts the state of the internal organ or blood flow of a patient by using ultrasonic waves, so as to examine and diagnose the internal organ or blood flow, a workflow system (also called "IASSIT: Intelligent Assistant System") in which, before the examination with the ultrasonic diagnostic equipment, a workflow expressing the procedure of the examination is defined as one (also called "workflow protocol") consisting of a plurality of items to-be-performed (also called "functional units" or "activities") executable by the ultrasonic diagnostic equipment, so as to control the operation of the ultrasonic diagnostic equipment in accordance with the workflow protocol during the examination, and a workflow editing system which serves to visually edit and create the workflow protocol for the workflow system, on the screen of the ultrasonic diagnostic equipment or an external computer.

BACKGROUND ART

An ultrasonic diagnostic equipment is an equipment wherein, on the basis of the ultrasonic pulse reflection method, ultrasonic wave signals are projected from the surface of the body of a patient toward a desired part within the body, the tomographic image of a soft tissue or blood flow information is noninvasively obtained using the information of reflected waves (ultrasonic echo signals) from the part. As compared with other medical image equipment including an X-ray diagnostic equipment, an X-ray CT scanner, an MRI, a nuclear medicine diagnostic equipment, etc., the ultrasonic diagnostic equipment has such merits as being small-sized and inexpensive, being capable of real-time display, affording a high safety without exposure to X-rays etc., and being capable of blood flow imaging, so that it is extensively utilized for diagnoses for the heart, the abdomen and the urinary organs and in obstetrics and gynecology, etc.

In order to meet such diagnostic needs, the ultrasonic diagnostic equipment has heretofore been furnished with functions which concern basic display modes in the cases of examinations and diagnoses, for example, the M-mode (displaying the temporal changes of reflected waves)/B-mode (displaying the tomographic image of an in vivo soft tissue) based on the ultrasonic pulse reflection method, the CW (continuous wave Doppler) mode/PW (pulsed Doppler) mode based on the ultrasonic Doppler method, and the CFM (color flow mapping) mode (color-displaying blood flow information in two dimensions on the tomographic image of the B-mode).

In recent years, with the advancements and betterments of image quality enhancing techniques, examining techniques with contrast agents, image processing techniques in 3D or the like, and so forth, the sorts of examining methods and clinical applications based on the ultrasonic diagnostic equipment have been diversified, and a large number of new functions complying with the methods and applications have come into practical use in addition to the functions concerning the image display as mentioned above.

Mentioned as the new functions are, for example, TDI (Tisse Doppler Imaging) wherein color speed information is superposed on a tissue echo part so as to image the movement of a tissue, THI (Tisse Harmonic Imaging) wherein a high-resolution image from which the artifact components of side lobes, multiple reflections, etc. have been cut is formed by employing harmonic waves in reflected waves without using any contrast agent, CHI (Contrast Harmonic Imaging) wherein, in order to image the situation of the flow of a contrast agent through a tissue, the image is formed by employing harmonic waves in reflected waves, a 3D display method wherein the 3D images of a tissue image (B-mode tomographic image) and a blood flow image (color Doppler angiographic image) are displayed or wherein the composite image of both the images is formed, and ACM (Automated Cardiac flow Measurement) wherein a cardiac output is automatically measured on the basis of color Doppler information.

With the diversification of such various functions of the ultrasonic diagnostic equipment as exemplified by TDI, THI, CHI, 3D display, ACM, etc., a very high degree of technique and experience have often been required for operations which are performed with input devices such as switches, a keyboard, a touch panel, a track ball and a mouse, by a technician, a doctor or the like user. There has been expected such an improper situation that the result of an examination differs depending upon the operating skill of the user, and the degradation of reliability attributed to the improper situation has been apprehended. On the other hand, the ultrasonic diagnostic equipments have been introduced, not only in large hospitals, but also in many hospitals, with the pervasion thereof owing to the cost curtailment thereof in recent years. For this reason, the population of users has increased more and more, and the proportion of users (beginners) unskilled in the operations tends to increase.

Under such a recent situation, accordingly, it is desired more than ever to provide an ultrasonic diagnostic equipment as to which even a beginner, for example, can master its operating method promptly and operate it easily.

As a relevant apparatus meeting such needs, there has been proposed, for example, a technique (workflow system) concerning the workflow navigation of an ultrasonic diagnostic equipment (JP-A-2001-137237). The workflow system is such that, before an examination, a workflow protocol which consists of a plurality of items to-be-performed called "activities" is created every examination type or every operator, and that, in case of the examination or a diagnosis, the activities are successively invoked and executed in accordance with the workflow protocol, whereby the operation of the ultrasonic diagnostic equipment is controlled along the desired steps of procedure of the examination.

According to the workflow system, there are expected such advantages that operations which require the skill or experience of a user can be automated, and that even an operator such as a beginner unskilled in the ultrasonic diagnostic equipment can master the operating method thereof promptly and more easily.

In the above workflow system, however, the job of creating a plurality of workflow protocols before examinations is necessitated. The job requires a predetermined programming ability and is liable to become complicated and troublesome for the operator, and the efficiency of the job is inferior. As a result, notwithstanding that the above advantages are expected, it has been apprehended that the workflow system will not be actually utilized.

DISCLOSURE OF THE INVENTION

The present invention has been made in view of the above circumstances, and has for its object to create a workflow protocol before an examination comparatively easily and promptly, in a workflow system wherein even a user such as beginner, who is slightly skilled in an ultrasonic diagnostic equipment and has experienced operations little, is permitted to master the operating method of the equipment promptly and to operate the equipment more easily.

In order to accomplish the object, the present invention has taken note of the construction of a system (visual editor) in which visual operations are possible on the basis of the GUI (graphical user interface) technology of a computer. According to the system, even a beginner user (end user) can intuitively and easily create a workflow protocol which is the core of the workflow system.

Besides, the creation of the workflow protocol is performed before the examination, but if necessary, the present invention adds the functions of simulating an examination time period required for performing the examination and computing the insurance points of the examination in accordance with the workflow protocol created beforehand. Owing to the functions, the information items of the simulated examination time period and the computed insurance points can be referred to, so that the more appropriate workflow protocol can be created in practical use.

The workflow system disclosed in JP-A-2001-137237 mentioned before is applied as a suitable example of the workflow system in the present invention. The terms of "workflow", "activity" and "workflow protocol" used in the description of the workflow system in this case shall be used as having substantially the same significances as those used in JP-A-2001-137237.

More specifically, the term "workflow" will be used as having the same significance as that procedure of an examination from the start to the end of the examination by an ultrasonic diagnostic equipment which is appropriately set every examination type or every operator.

Besides, the term "activity" will be used as having the same significance as a program which is assigned to a plurality of operating items (patient registration, scan, measure, print, save, etc.) that are executed along the workflow by the ultrasonic diagnostic equipment, and which controls the operation of the ultrasonic diagnostic equipment in accordance with the set contents of the operating items. Mentioned as the program forming the activity is, for example, ActiveX Control (Microsoft Corporation in US) which is described in a programming language for software development, such as C++ or Visuual Basic, or a program component which utilizes the JAVA technology.

Further, the term "workflow protocol" will be used as having the same significance as data which define the workflow by using the activities. The data forming the workflow protocol are constructed of, for example, source program data in an intermediate language, the XML (extensible Markup Language), or the like.

Here in this specification, the "workflow system" in the present invention shall be used as a concept which includes, not only the workflow system mentioned above, but also systems utilizing the workflow navigation techniques of medical image diagnostic equipment, for example, an equipment that permits a user to make a diagnosis utilizing an ultrasonic diagnostic equipment, easily in accordance with an appropriate procedure and appropriate contents, an equipment that can offer the optimal support information concerning a diagnostic job, and an equipment that can check whether or not a diagnosed result or the like is appropriate.

An ultrasonic diagnostic equipment according to the present invention completed on the basis of the idea as stated above consists in an ultrasonic diagnostic equipment which projects ultrasonic signals into a patient, and which generates an ultrasonic image on the basis of reflection echoes from within the patient, comprising control means for controlling equipment operations including the generation of the ultrasonic image, in accordance with a workflow protocol based on an examination procedure of steps created beforehand; and workflow edit means configured so as to visually edit the workflow protocol on a screen.

The workflow visual edit means should appropriately include at least one of the function of simulating an examination time period in accordance with the workflow protocol, the function of computing insurance points relevant to an examination in accordance with the workflow protocol, and the function of saving the workflow protocol in a predetermined file format (for example, XML format). Besides, the workflow visual edit means should preferably be installed so as to be operable by both the ultrasonic diagnostic equipment and a computer apparatus connected outside the equipment.

In addition, a workflow edit system according to the present invention comprises means for displaying icons on a screen, for activities which are defined as functional units of an examination procedure of steps; means for moving the icons and arraying them in a predetermined order through user operations (including, for example, drag & drop operations), thereby to form a workflow on the screen; and means for saving the workflow in a predetermined format which is executable by an ultrasonic diagnostic equipment.

Further, a method of controlling an ultrasonic diagnostic equipment according to the present invention consists in a control method which projects ultrasonic signals into a patient, and which forms an ultrasonic image on the basis of reflection echoes from the patient, characterized by comprising the step of displaying a list of activities which are defined as functional units of an examination procedure of steps, and defined contents of a workflow protocol in which the plurality of activities are arrayed in a sequence of execution of the activities, on an identical screen by using icons; the step of adding the activities within the list, to the defined contents by drag & drop operations; and the step of saving the resulting defined contents in a form which is executable by the ultrasonic diagnostic equipment.

It is favorable that the list displays the activities in group units, and that the groups are changed-over by selecting a group list part on the screen.

BRIEF DESCRIPTION OF THE DRAWINGS

FIG. 8(a) is a diagram showing a display example of a tool menu on the workflow edit screen, while FIG. 8(b) is a diagram for explaining the functions of the individual tool buttons of the tool menu.

FIGS. 12(a) and (b) are diagrams showing display examples of a menu bar on the workflow edit screen, while

FIG. 32 is a diagram for explaining a setting example of the execution attribute of an activity.

FIG. 33 is a diagram for explaining a method of setting the attributes of each individual activity.

BEST MODE FOR CARRYING OUT THE INVENTION

Now, an ultrasonic diagnostic equipment, a workflow editing system, and a method of controlling the ultrasonic diagnostic equipment, according to one embodiment of the present invention, will be concretely described with reference to the accompanying drawings.

Figure 1:
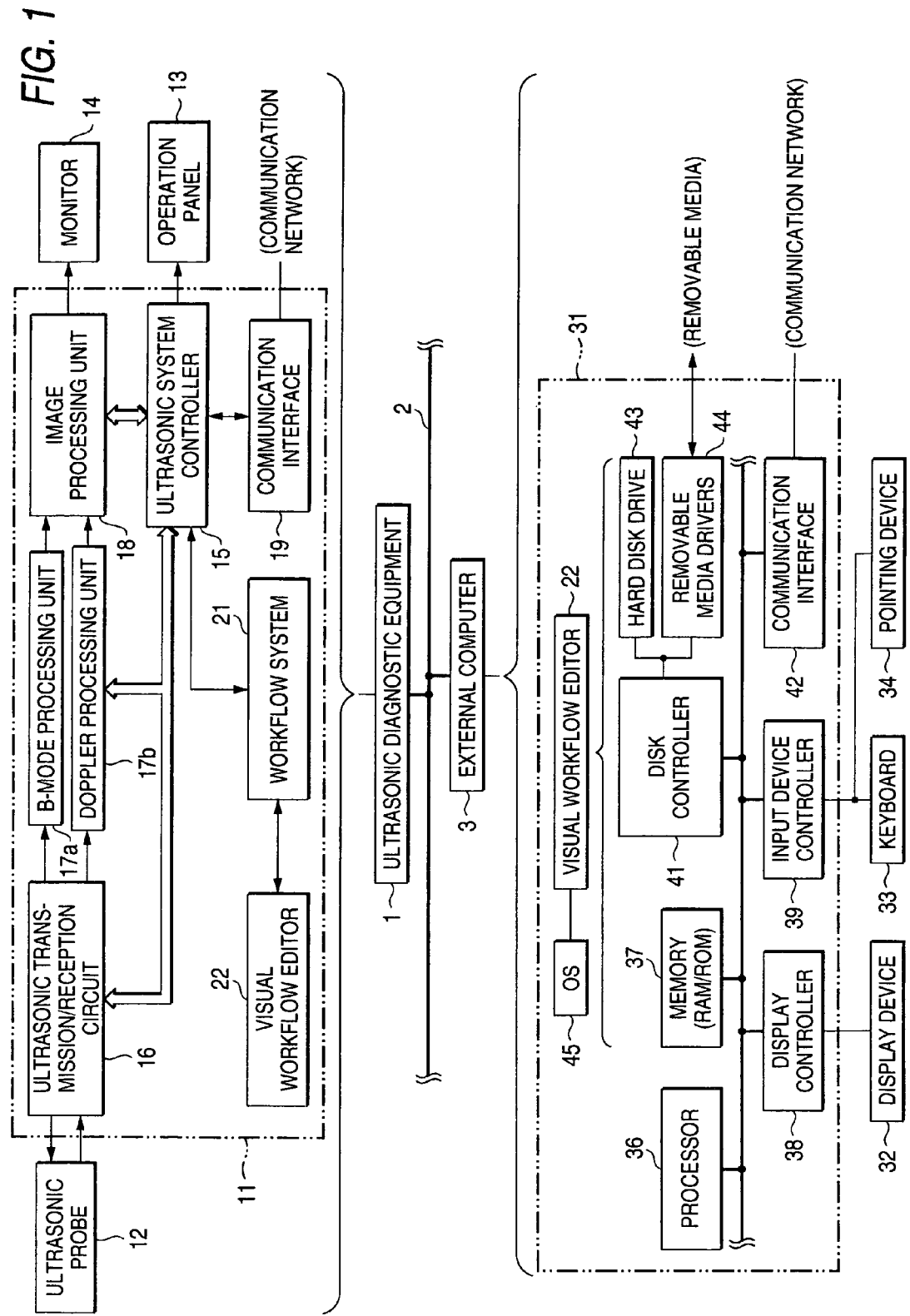
FIG. 1 is a schematic block diagram showing the general configuration of a medical image diagnosis system in which an ultrasonic diagnostic equipment, and a visual editor (visual workflow editor) being a workflow editing system according to an embodiment of the present invention are installed.

FIG. 1 shows the outline of a medical image diagnosis system which comprises the ultrasonic diagnostic equipment 1 according to this embodiment, and an external computer 3 that is communicably connected to the ultrasonic diagnostic equipment 1 through a communication network (hereinbelow, simply termed "network") 2 such as LAN (local area network) The network 2 here includes, not only a LAN in facilities such as a hospital, but also a wide-area computer network such as the Internet, which is available in conformity with a predetermined communication protocol (such as TCP/IP) through a communication network (including also a radio channel) such as dedicated line or public network.

In the medical image diagnosis system shown in FIG. 1, a workflow system 21 according to this embodiment is installed in the ultrasonic diagnostic equipment 1 so as to be executable, while a visual workflow editor (hereinbelow, shortly termed "visual editor") 22 which is a workflow editing system according to this embodiment is installed so as to be executable in the ultrasonic diagnostic equipment 1 and the external computer 3, respectively.

By way of example, the ultrasonic diagnostic equipment 1 has functions for obtaining the B-mode tomographic image and CFM (color flow mapping) image of a patient, and the hardware architecture thereof includes the equipment proper 11, and an ultrasonic probe 12, an operating panel 13 and a monitor 14 which are connected to the equipment proper 11, as shown in FIG. 1.

The operating panel 13 is furnished with operating devices such as buttons, a keyboard, a track ball and a mouse. The operating devices are used in order that an operator may enter or instruct the inputs or settings of information necessary for a measurement or analysis, such as patient information, equipment control conditions, desired image conditions and an ROI (region of interest), the selection or setting of a display mode (such as B-mode or CFM-mode), various operations or settings in the case of utilizing the workflow system 21, and so forth.

The ultrasonic probe 12 is a device (probe) which takes charge of transmitting/receiving ultrasonic wave signals projected/reflected between this probe and the patient, and it is formed of piezoelectric elements of piezoelectric ceramics as are electrical/mechanical reversible transducer. By way of example, the probe 12 is configured of one of the phased array type in which a plurality of arrayed piezoelectric elements are disposed at a front end part. Thus, the probe 12 converts pulse drive voltages fed from the equipment proper 11, into the ultrasonic pulse signals and transmits the signals in a desired direction within the scan region of the patient, while it converts the ultrasonic wave signals reflected from the patient, into echo signals of corresponding voltages.

The equipment proper 11 includes, not only an ultrasonic system controller 15 which serves as the control center of the whole ultrasonic diagnostic equipment 1, but also several units which operate under the control of the controller 15, that is, an ultrasonic transmission/reception circuit 16 which is connected to the ultrasonic probe 12, a B-mode processing unit 17a and a CFM (color flow mapping) processing unit 17b which are connected to the side of the transmission/reception circuit 16 for outputting an ultrasonic reception signal, an image processing circuit 18 which is connected to the output sides of both the processing units 17a, 17b, and a communication interface 19 which is connected to the communication network 2. In addition, the workflow system 21 and the visual editor 22 are respectively installed in the equipment proper 11 as stated before.

An example of the transmission/reception circuit 16 has, for example, a pulse generator, a transmission delay circuit and a pulser on its transmission side, and for example, a preamplifier, an A/D converter, a reception delay circuit and an adder on its reception side. Owing to this configuration, in the transmission/reception circuit 16, drive signals are sent to the individual piezoelectric elements of the ultrasonic probe 12 at timings endowed with predetermined transmission delay times for respective transmission channels on the transmission side, in accordance with the display mode, such as B-mode or CFM mode, which has been selected by the operator through, for example, the operating panel 13 under a control signal based on the ultrasonic system controller 15, whereby the ultrasonic wave signals are transmitted from the individual piezoelectric elements of the ultrasonic probe 12 toward the interior of the patient. On the other hand, the transmission/reception circuit 16 receives the ultrasonic echo signals which contain components reflected from the mismatching surfaces of acoustic impedances within the patient and scattered by scatterers within tissues in response to the transmission of the ultrasonic wave signals, as echo signals of corresponding voltage magnitudes through the individual piezoelectric elements of the ultrasonic probe 12, and it subjects the echo signals to reception delay and addition processing, so as to output the processed reception signal to the B-mode processing unit 17a and the CFM processing unit 17b of the succeeding stage, respectively.

The B-mode processing unit 17a subjects the reception signal from the transmission/reception circuit 16 to envelope detection, and it outputs the signal thus detected, to the image processing circuit 18 as bearing the form information of the tissues in the patient (image data of a B-mode image) Besides, the CFM processing unit 17b performs the frequency analysis of speed information on the basis of the electric signal received from the transmission/reception circuit 16, and it outputs the analytical result to the image processing circuit 18 as a signal bearing the moving speed information of a blood flow or the tissues within the patient (image data of a CFM image).

The image processing circuit 18 receives the signals from the B-mode processing unit 17a and the CFM processing unit 17b, it performs image processing, in which various images concerning the B-mode image and the CFM image are formed and are superposed or arrayed in accordance with the various settings of the display mode, a diagnosis mode, a measurement, an analysis, etc. selected through the operating panel 21 by the operator under the control of the ultrasonic system controller 15, and in which various quantitative analyses or measurements are performed on the basis of the images so as to add information indicative of the results onto the images, and it converts the processed image signals into scan signals for TV and outputs the scan signals to the monitor 13. Thus, the various images concerning the B-mode image and the CFM image, the information concerning the results of the measurements and analyses thereof, and so forth are displayed on the monitor 13.

Besides, in case of utilizing the workflow system 21 to be stated later, the image processing circuit 18 converts image signals which form various screens (refer to later description) concerning the workflow system 21 on the basis of the operator's instructions inputted through the operating panel under the control of the ultrasonic system controller 15, into scan signals for TV and outputs the scan signals to the monitor 13 so as to display the screens on the display screen of the monitor.

By way of example, the ultrasonic system controller 15 has the functions of a computer which includes a CPU (processor), a memory (RAM/ROM), a hard disk drive, drivers for removable media (such as a CD-ROM, a floppy disk and a memory card), etc. that are connected to an internal bus not shown, and it controls the operation of the whole ultrasonic diagnostic equipment 1 in accordance with preprogrammed procedures in a diagnosis or examination mode. The control operation is performed on the basis of the diagnosis or examination mode, transmission/reception conditions, the display mode, transmission conditions, reception conditions, conditions for executing the workflow system 21, etc. as instructed through the operating panel 13 by the operator.

The workflow system 21 is constructed of application software which controls the operation of the ultrasonic diagnostic equipment 1 through, for example, the processing of the ultrasonic system controller 15. The software constructing the workflow system 21 is constituted by, for example, a plurality of modules which form programs or data, and it is offered by a computer-readable record medium such as CD-ROM, floppy disk, hard disk or memory card, or via the network 2.

Insofar as the external computer 3 is a computer apparatus communicable with the ultrasonic diagnostic equipment 1 through the communication network 2, it may be of any type, for example, a dedicated workstation installed in a hospital or a general-purpose PC (personal computer). In this embodiment, the PC is taken as an example (hereinbelow, called "external PC").

As shown in FIG. 1, the external PC 3 has the apparatus proper 31, a display device 32, a keyboard 33, and a pointing device 34 such as mouse, as an example of the hardware architecture thereof. In the apparatus proper 31, a processor (CPU) 36, a memory (RAM/ROM) 37, a display controller 38 for the display device 32, an input device controller 39 for the input devices (keyboard 33 and pointing device 34), a disk controller 41 and a communication interface 42 are connected through a bus 35, and a hard disk drive 43 and removable media drivers 44 are further connected through the disk controller 41.

A magnetic disk (such as floppy disk), an optical disk (such as CD-ROM), and a magnetooptical disk (such as MO) are exemplified as the removable media which are driven by the removable media drivers 44.

Besides, regarding the external PC 3, an OS (operating system) 45 such as the Windows type OS of Microsoft Corporation in US, or a UNIX type OS (e.g., Linux), and various sorts of application software which operate on the OS 45, are included as the example of the software which form instructions to be executed by the processor 36, and data. The software includes one which constructs the same visual editor 22 (refer to later description) as that of the ultrasonic diagnostic equipment 1 described above.

Figure 2:
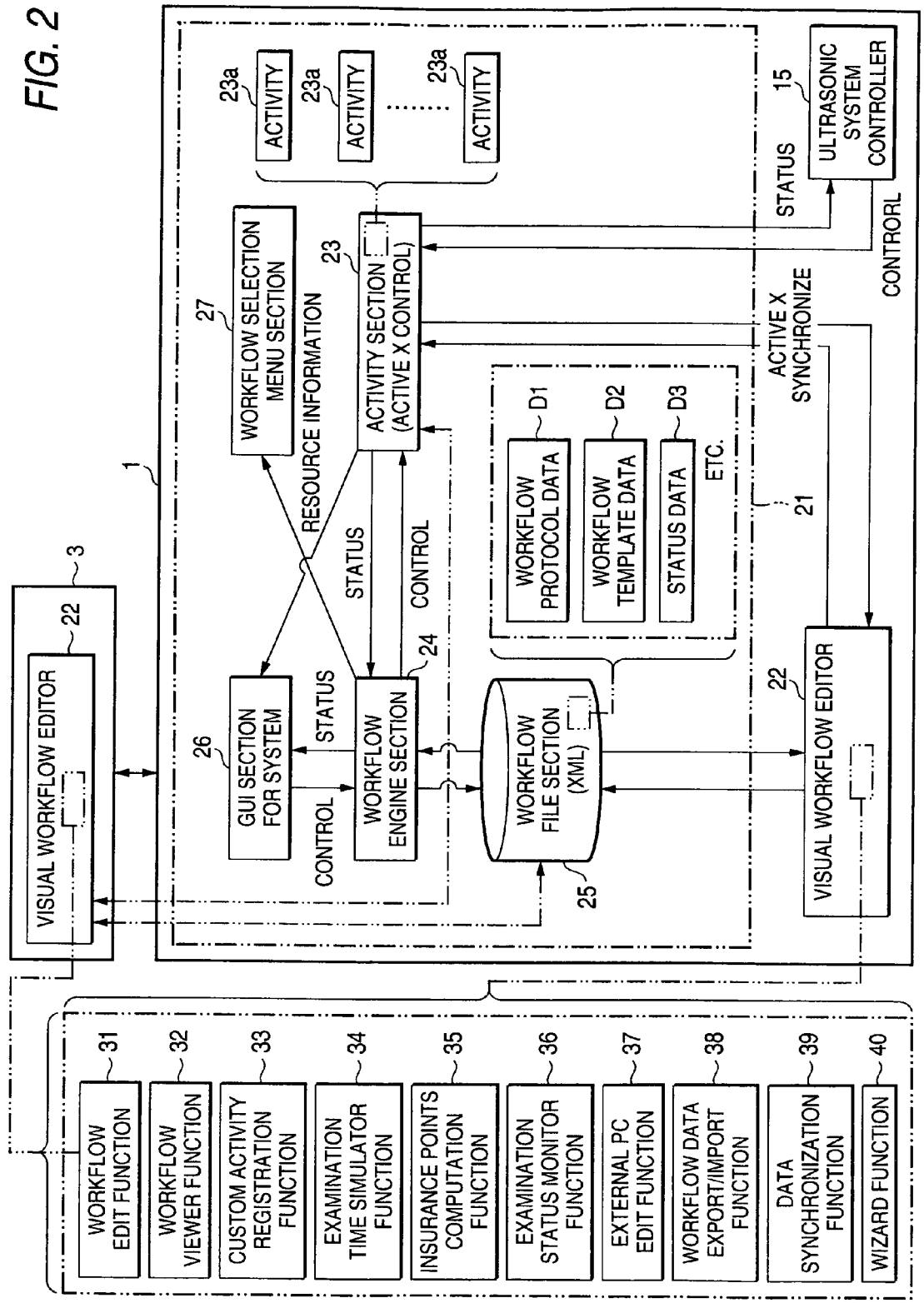
FIG. 2 is a schematic block diagram showing examples of functional configurations of the workflow system and the visual editor.

FIG. 2 illustrates examples of the software (functional) configurations of the workflow system 21 and the visual editor 22.

In the workflow system 21 shown in FIG. 2, an activity module (hereinbelow, "activity section 23"), a workflow engine module (hereinbelow, "workflow engine section 24"), a workflow file module (hereinbelow, "workflow file section 25"), a GUI (graphical user interface) module for IASSIT (hereinbelow, "GUI section for system, 26"), and a workflow selection menu module (hereinbelow, "workflow selection menu section 27") are included as the module configuration which forms the software.

The activity section 23 has a plurality of activity programs (hereinbelow, shortly termed "activities 23a-23a") which function as, for example, ActiveX control, and it is capable of performing such processing as activating the individual activities 23a-23a in accordance with controls from the workflow engine section 24 and the ultrasonic system controller 15, and executing such processing as offering various statuses to the workflow engine section 24 and the ultrasonic system controller 15 and offering resource information to the GUI section 26 for the system. Besides, the activity section 23 is capable of synchronizing predetermined data between it and the visual editor 22 (including that installed in the external PC 3) by, for example, an ActiveX synchronize function.

The workflow engine section 24 is capable of such processing as receiving statuses concerning current situations between it and the individual modules (the activity section 23, workflow file section 25, GUI section 26 for the system, workflow selection menu section 27, etc.), and controlling the various operations between it and the individual modules (for example, the activity execution operation between it and the activity section 23, the workflow data read/write operation between it and the workflow file section 25, and the screen display operation between it and the GUI section 26 for the system).

The workflow file section 25 has workflow data in a predetermined file format (for example, XML format) (workflow protocol data D1, workflow template data D2, status data D3, etc.), and it is capable of executing processing concerning the file management of the workflow data (such as read/write), between it and the workflow engine section 24 and the visual editor 22.

Among the workflow data here, the workflow protocol data D1 stipulate workflows by the plurality of activity programs 23a-23a. In this example, the workflows include, not only ones which are registered as manufacturer default (initialization) beforehand, but also ones which are edited and created, and additionally registered (user registration) or revised by the visual editor 22.

Besides, the workflow template data D2 register templates as manufacturer default (initialization) and capable of reutilizing the workflow protocol data D1. In this example, the templates include, not only ones which are registered as manufacturer default (initialization) beforehand, but also ones which are edited and created, and additionally registered (user registration) or revised by the visual editor 22.

The status data D3 include the contents of a workflow, a subworkflow, etc. and information necessary for notifying the proceeding situations to the operator, and such information as the names of the workflow and its activities, the current proceeding situations thereof (such as normal, continue and quit), the start and end times thereof, and time periods required for executing the individual activities.

The GUI section 26 for the system forms an interface with the operator, and it includes various screens concerning the workflow system 21 as are displayed on the monitor 14 through the image processing circuit 18 of the ultrasonic diagnostic equipment 1 under the control of the ultrasonic system controller 15, for example, a menu screen on which the plurality of activities 23a-23a are displayed as icon AP-AP (refer to later description) indicated by "icons (patterns) "+"names" for easily understanding the functions of the activities, or the images of character strings.

The workflow selection menu section 27 is capable of executing processing in which a menu capable of selecting a workflow or the like is displayed on the monitor 14 of the ultrasonic diagnostic equipment 1 through the processing of the GUI section 26 for the system.

As stated before, the visual editors 22 are installed in both the ultrasonic diagnostic equipment 1 and the external PC 3, and it offers an operating environment in which the operator including an end user assembles and edits a workflow visually by drag & drop operations, etc. while watching an icon, characters etc. displayed on the screen of the monitor 14 or the display device 32.

Now, the details of the visual editor 22 will be described with reference to the accompanying drawings.

1. Basic Configuration of Visual Editor

The functions of the visual editor 22 are incarnated by the processing of computers which execute the instructions of the programs of this visual editor (for example, the ultrasonic system controller 15 in the ultrasonic diagnostic equipment 1, and the processor 36 of the external PC 3). As shown in FIG. 2 by way of example, the functions include a workflow edit function 31, a workflow viewer function 32, a custom activity registration function 33, an examination time simulator function 34, an insurance points computation function 35, an examination status monitor function 36, an external PC edit function 37, a workflow data export/import function 38, a data synchronization function 39, and a wizard (help) function 40.

The workflow edit function 31 is so configured that workflow data (workflow protocol data D1, workflow template data D2) are visually edited using icons or patterns expressive of the activities 23a (for example, activity icons to be stated later), on the screen of the monitor 14 of the ultrasonic diagnostic equipment 1 or the display device 32 of the external PC 3 (a workflow edit screen to be stated later).

The basic operation of the workflow editing is performed in such a way that icons corresponding to the activities 23a-23a are arrayed and have their order determined by drag & drop operations which employ the operating panel 13 of the ultrasonic diagnostic equipment 1 or the pointing device such as the mouse of the external PC 3 (refer to later description)

The workflow data D1, D2 created and edited by the workflow edit function 31 are stored in the workflow file section 25 of the workflow system 21 via the network or via the removable medium, and they are read out by the workflow engine section 24 at the operation of the workflow system 21, etc.

The workflow viewer function 32 lists and displays all the contents of the workflows edited by the workflow edit function 31 on the screen of the monitor 14 of the ultrasonic diagnostic equipment 1 or the display device 32 of the external PC 3 (refer to a workflow viewer screen W21 to be stated later) so that the operator may understand the contents. By way of example, the contents are displayed in a tree form, or they are listed and displayed within individual hierarchical levels.

The custom activity registration function 33 is so configured that the operator create and register the activities 23a originally.

The examination time simulator function 34 is so configured that an examination time period required in a case where a workflow edited and designed through the workflow edit function 31 by the operator is actually executed in a diagnosis or examination are estimated (simulated) beforehand, and that required time periods are set in, for example, units of the activities 23a beforehand, whereby the total time period thereof can be computed.

The examination points computation function 35 estimates insurance marks in the case of employing the workflow designed with the workflow edit function 31, from this workflow. By way of example, it can set the insurance points in units of the activities and compute the total insurance points thereof.

The examination status monitor function 36 is so configured that, in a case, for example, where the ultrasonic diagnostic equipment 1 connected on the communication network 2 is executing the workflow system 21, status information concerning the situation of the execution can be monitored on the screen of the monitor 14 of another ultrasonic diagnostic equipment 1 on the communication network 2 or the display device 32 of the external PC 3 (examination status screen W30 to be stated later).

The external PC edit function 37 is so configured that the visual editor 22 is operated, not only by the ultrasonic diagnostic equipment 1, but also by the external PC 3.

The workflow data export/import function 38 is so configured that the workflow data edited and created with the workflow edit function 31 are exported/imported to/from the hard disk, for example, in the ultrasonic diagnostic equipment 1 or another computer (such as PC) such as the external PC 3. The file format of the workflow data D1, D2 in this case is, for example, the XML format.

The data synchronization function 39 is so configured that data concerning the activities 23a are synchronized between the ultrasonic diagnostic equipment 1 and the external PC 3, so as to check the program versions of the activities 23a and to support data synchronization in both the aspects via the network and via the medium.

The wizard function 40 is so configured as to automatically create a workflow template merely in such a way, for example, that the operator inputs the purpose of an examination on a predetermined screen.

2. Screen Configurations of Visual Editor

Here, examples of the screen configurations of the visual editor 21 offered by the above functions 31-40 will be described.

Figure 3:
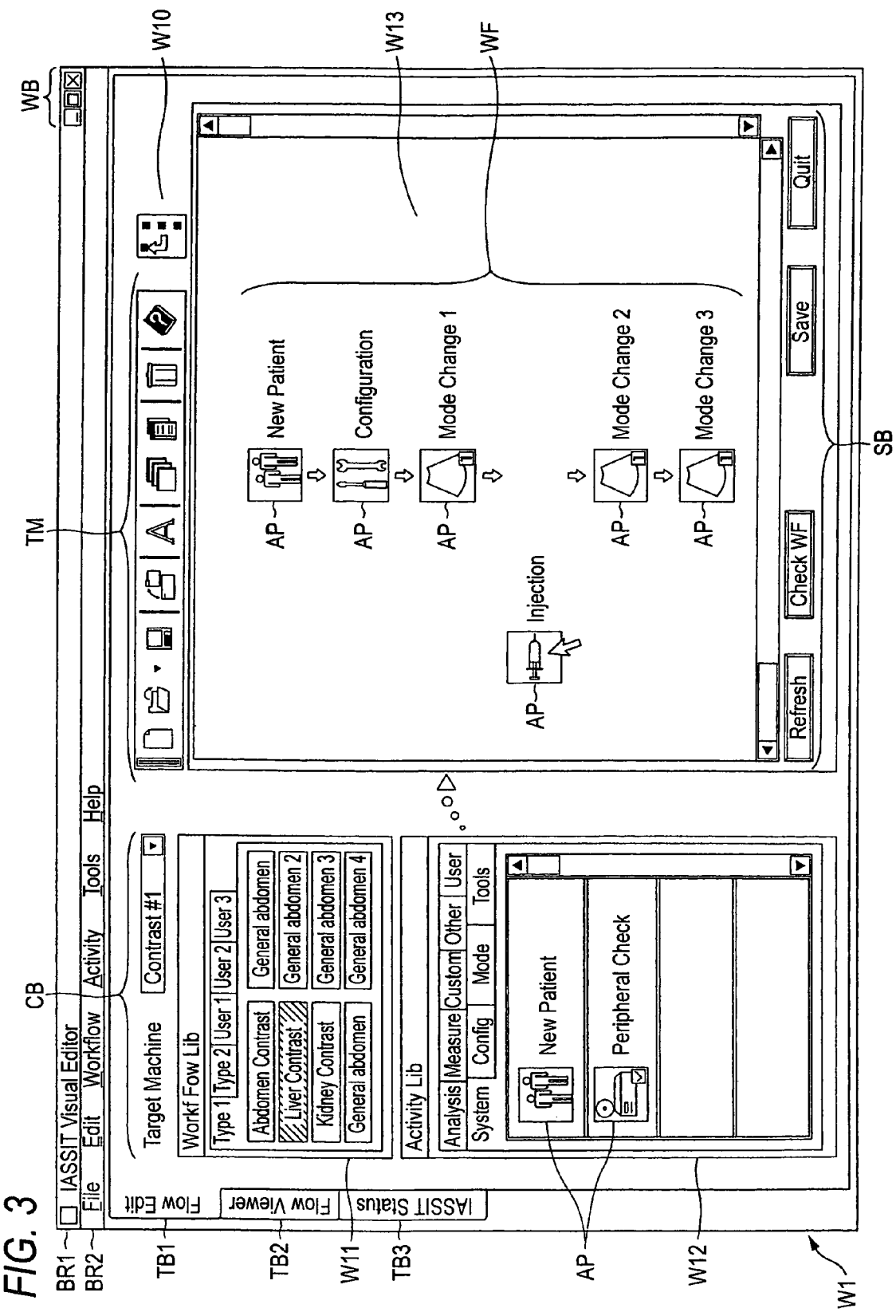
FIG. 3 is a diagram showing a display example of the initial screen (workflow edit screen) of the visual editor.

FIG. 3 shows an example of a GUI screen W1 being an initial screen under a GUI operating environment, which is displayed on the monitor 14 of the ultrasonic diagnostic equipment 1 or the display device 32 of the external PC 3 in activating the visual editor 21.

In the GUI screen W1, a bar (title bar) BR1 which displays the system registration title of the visual editor 21 (in this embodiment, "IASSIT (Intelligent Assistant System) Visual Editor" by way of example) by an icon and characters and which lays out predetermined screen control buttons (several control buttons for the minimization, maximization, restoration, closing, etc. of the screen) WB, and a bar (menu bar) BR2 which displays a menu concerning the operation of the visual editor 21 (menu items of "File", "Edit", "Workflow", "Activity", "Tools" and "Help"), are laid out at appropriate positions, for example, on the upper side of the screen.

Besides, in the GUI screen W1, three screen changeover tabs ("Flow edit tab TB1", "Flow viewer tab TB2" and "IASSIT status tab TB3") are set at appropriate positions, for example, the middle—lower sides of the screen, and three screens ("Workflow edit screen W10", "Workflow viewer screen W20" and "Examination status monitor screen W30") can be changed-over and displayed in accordance with the tabs. In the example in FIG. 3, the workflow edit screen W10 is displayed by the selection of the flow edit tab TB1.

The workflow edit screen W10 is offered by the workflow edit function 31. It is so configured that, as shown in FIG. 3, such a job as arranging (moving and positioning) icons AP- AP expressive of the activities 23a by icon moving operations, etc. which are intuitive and visual operations, such as the drag & drop operations of the mouse, performed while the operator watching the screen, can be executed, whereby a workflow WF is visually edited.

In the workflow edit screen W10, as shown in FIG. 3, not only "Workflow library screen W11", "Activity library screen W12" and "Workflow design screen W13", but also "Tool menu TM", "Shortcut buttons SB" and "Target machine selecting box (combo box) CB" are laid out and displayed at appropriate positions. Although not shown in this example, "Popup menu", "Help screen", etc. to be described later can also be displayed by mouse operations, etc.

Figure 4:
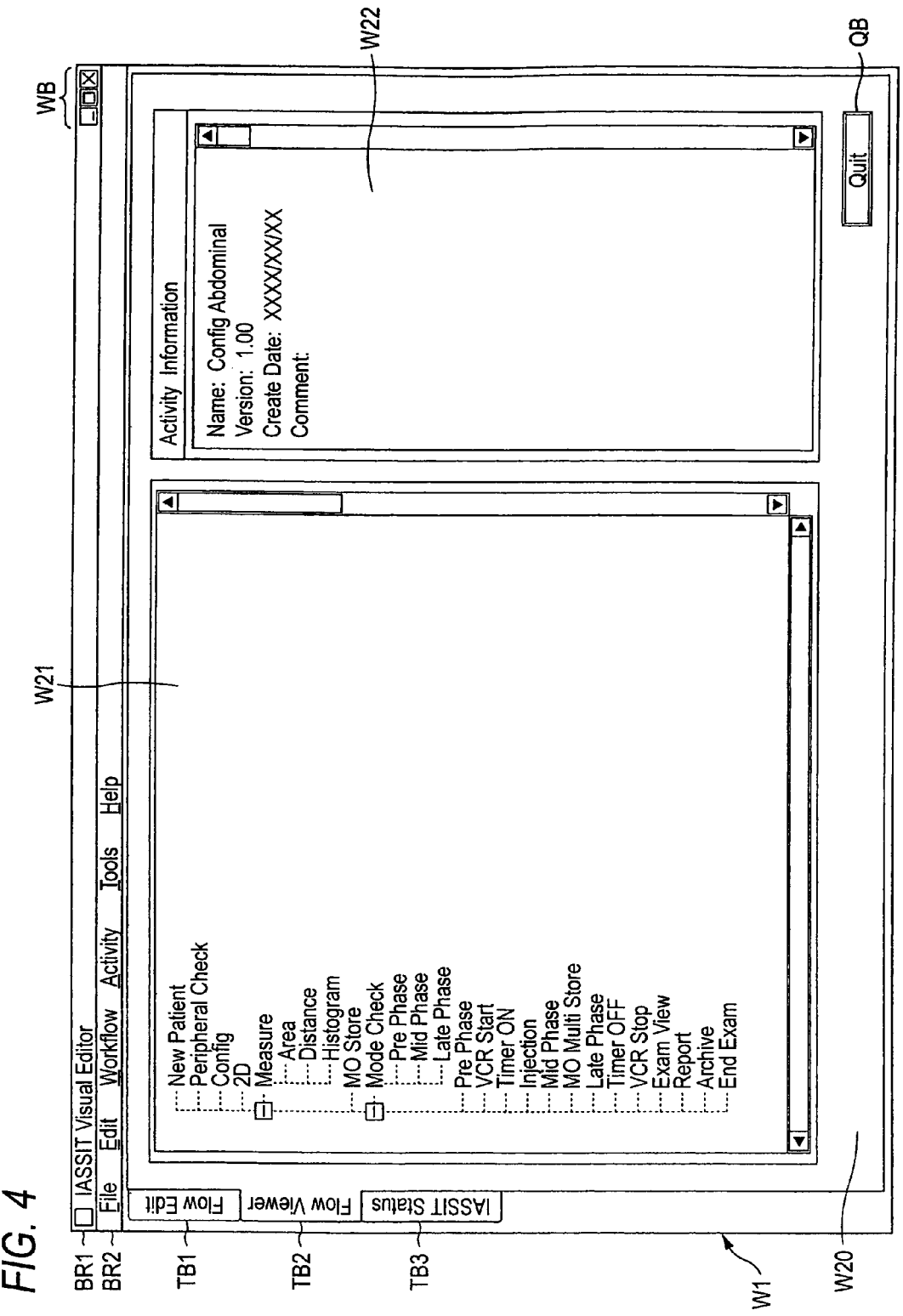
FIG. 4 is a diagram showing a display example of the workflow viewer screen of the visual editor.

FIG. 4 shows an example of the workflow viewer screen W20. The workflow viewer screen W20 is displayed when changed-over from the workflow edit screen W10 or the examination status monitor screen W30 by the selection of the flow viewer tab TB2 on the GUI screen W1.

The workflow viewer screen W20 is offered by the flow viewer function 32, and it is so configured as to list and display all the contents of a workflow designed on the workflow edit screen W10, including an activity at the lower hierarchical level thereof. In the example of FIG. 4, "Workflow list display screen W21", "Activity information display screen W22" and "Quit button QB" are laid out at appropriate positions.

Figure 5:
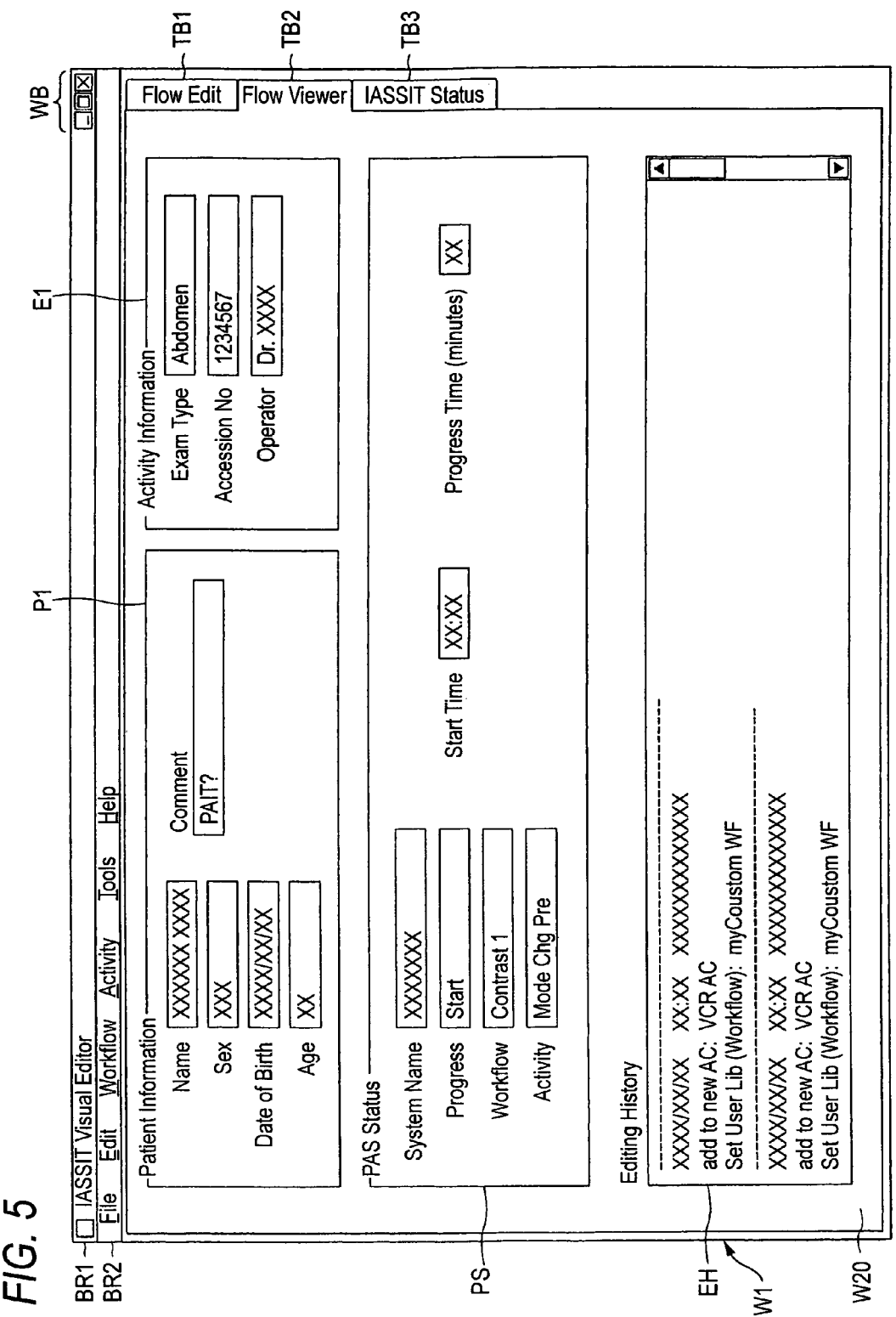
FIG. 5 is a diagram showing a display example of the examination status monitor screen of the visual editor.

FIG. 5 shows an example of the examination status monitor screen W30. The examination status monitor screen W30 is displayed when changed-over from the workflow edit screen W10 or the workflow viewer screen W20 by the selection of the status tab TB3 on the GUI screen W1.

The examination status monitor screen W30 is offered by the examination status monitor function 33, and it is so configured that the various information items of the workflow system 21, which is under execution in another host system (another ultrasonic diagnostic equipment 1) connected on the communication network 2, are monitored and displayed via the communication network 2.

In the example of FIG. 5, on the examination status monitor screen W30, patient information (such as name, sex, date of birth, sex, and comment) PI, examination information (examination type, doctor in charge) EI, system status information to be monitored (such as system name, current examination progress situation (start, end, etc.), start time, progress time, workflow type currently under use, and activity type currently under use) PS, history information on registration, deletion, etc. (such as date and hour at which a workflow was edited (for addition, deletion and revision), title of the workflow, date and hour of the user registration of the workflow or activity, title of the added workflow or activity, date and hour at which the equipment was synchronized with an external equipment, names of devices which are subjects for a synchro mode or the synchronization) ED, and so forth are respectively displayed at appropriate positions.

Next, detailed configurational examples on the workflow edit screen W10 will be described.

Figure 6:
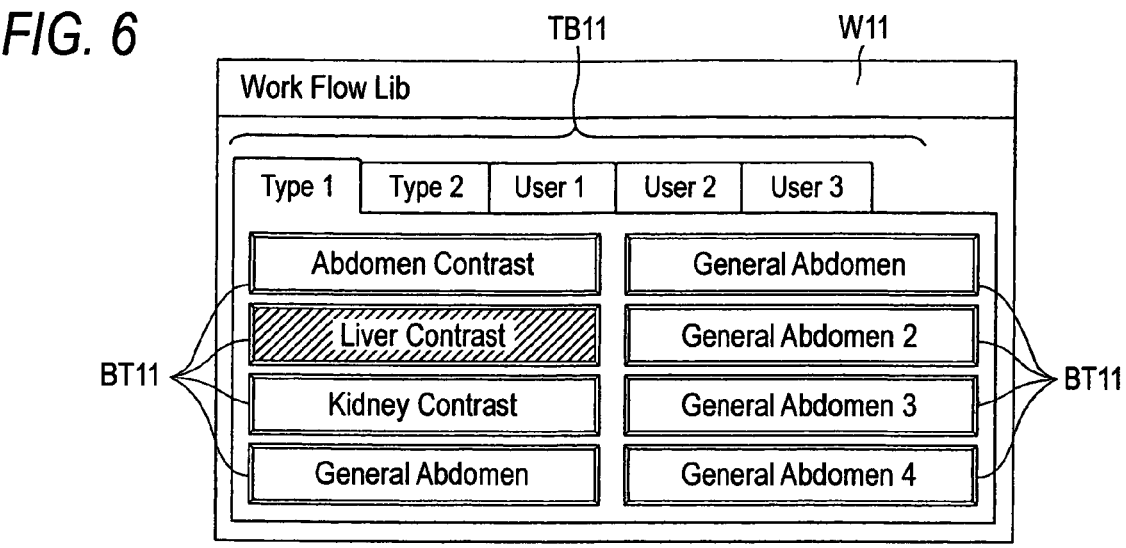
FIG. 6 is a diagram showing a display example of a workflow library screen on a workflow edit screen.

FIG. 6 shows the configurational example of the workflow library screen W11 on the workflow edit screen W10. The workflow library screen W11 in this example is so displayed that workflow template data registered as manufacturer default (initialization) or created by the operator can be selected as a plurality of buttons BT11 on pages within tab cards TB11 respectively for a plurality of categories (in the illustrated example, the categories of "Type 1", "Type 2", "User 1", "User 2" and "User 3").

The workflow template data as the manufacturer default are registered in the categories of Types 1 and 2 among the tab cards TB11, while the workflow template data created with the visual editor 22 by the operator are registered in the categories of Users 1-3 (in this case, it should preferably be set that the deletion of, for example, the workflow template data of user registration and the manufacturer default in the categories of Types 1 and 2 is impossible).

In the example of the workflow library screen W11 as shown in FIG. 6, the workflow template data D2 of the manufacturer default as registered in the tab card TB11 of Type 1 are exemplified, and the names of workflows (for example, workflow templates for an abdomen contrast echo examination, a liver contrast echo examination, a kidney contrast echo examination, and five sorts of general abdomen examinations) are displayed.

On the workflow library screen W11 shown in FIG. 6, the operator selects a desired workflow template through the click operation of the mouse, or the like, whereby the selected workflow template data D2 can be displayed in the workflow design screen W13 on the workflow edit screen W10.

Figure 7:
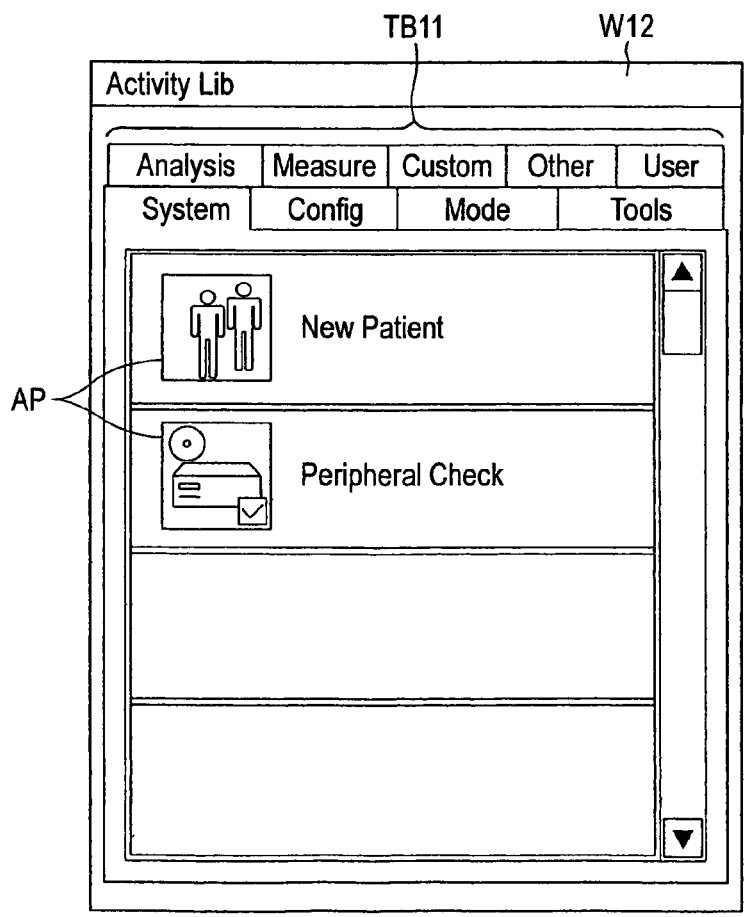
FIG. 7 is a diagram showing a display example of an activity library screen on the workflow edit screen.

FIG. 7 shows the configurational example of the activity library screen W12 on the workflow edit screen W10. The activity library screen W12 in this example is a screen form which is managing the activities 23a, and it is so displayed that icons which correspond to the activities 23a conforming to respective categories (hereinbelow, termed "activity icons") AP can be selected on pages within tab cards TB12 respectively for a plurality of categories (in the illustrated example, the categories of "System", "System configuration", "Mode", "Roots", "Analysis", "Measurement", "Custom", "Other" and "User"), in the format of "icon"+"name" by drag & drop operations.

The activity icons AP in the number of, for example, four are displayed on one page within the tab cards TB12. In a case where five or more icons AP are registered on one page, they can be displayed by vertically moving the page with a scroll bar or scroll buttons located on the left side of the screen. Incidentally, the activity icons AP as manufacturer default are usually registered in the categories except "User" among the tab cards TB12, while the activity icons AP created by the operator are registered in the "User" category.

In the example of the activity library screen W12 as shown in FIG. 7, the activity icons AP of the manufacturer default as registered in the tab card TB12 of "System" (for example, a new patient, and the check of a peripheral device (such as MO)) are exemplified.

On the activity library screen W12 shown in FIG. 7, the operator can select a desired activity icon AP through the click operation of the mouse, or the like, and move the selected icon AP into the workflow design screen W13 on the workflow edit screen W10 through the drag & drop operations of the mouse so as to arrange it at an appropriate position for configuring the workflow WF.

Figures 8A, 8B:
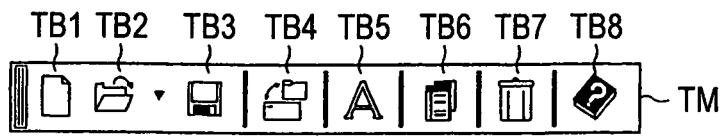

FIGS. 8(a) and (b) show an example of the tool menu TM on the workflow edit screen W10. As shown in the figures, tools necessary for editing are collectively displayed on the tool menu TM in this example.

Concretely, there are exemplified a tool button TB1 for creating a workflow anew, a tool button TB2 for loading the workflow data D1, D2 saved in the local disk, a tool button TB3 for saving the workflow data D1, D2, a tool button TB4 for exporting the workflow data D1, D2 in order to utilize these data D1, D2 in the visual editor 22 on another ultrasonic diagnostic equipment 1 or the external PC 3, a tool button TB5 for creating a subworkflow (refer to later description) WF, a tool button TB6 for entering comments, a tool button TB7 for deleting a selected object, and a tool button TB8 for displaying help.

The display/nondisplay of the tool bar of the tool menu TM can be set by the "Option" (GUI: option dialog editor) of the "Tool" menu M5 in the menu bar BR as will be stated later.

Figure 9:
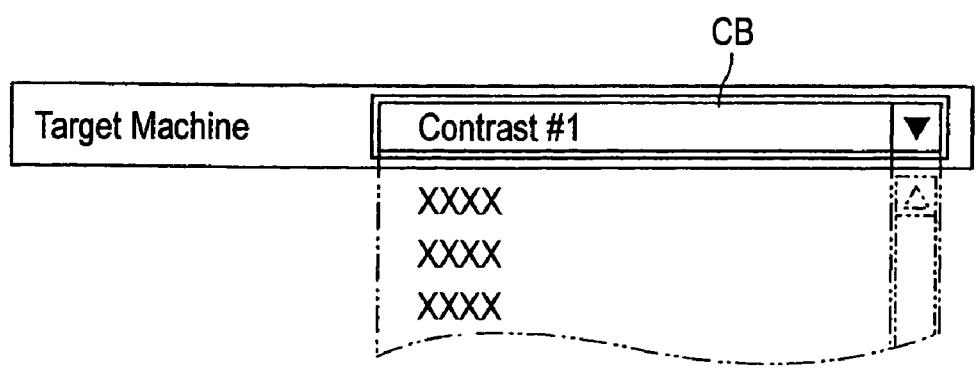
FIG. 9 is a diagram showing a display example of a target machine selecting box on the workflow edit screen.

FIG. 9 shows an example of the target machine selecting box CB on the workflow edit screen W10. The name of the ultrasonic diagnostic equipment 1 capable of network mounting (in the illustrated example, "Contrast #1") is displayed in the target machine selecting box CB in this example. On the target machine selecting box CB, a device to be mounted can be changed-over through the user's selection operation.

Figure 10:
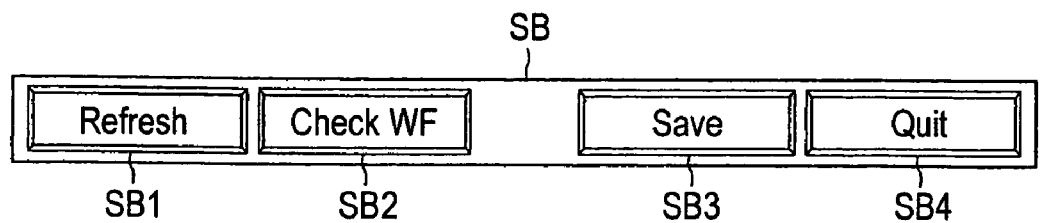
FIG. 10 is a diagram showing examples of shortcut buttons on the workflow edit screen.

FIG. 10 shows examples of the shortcut buttons SB on the workflow edit screen W10. As the shortcut buttons SB in this example, a "Workflow check" button SB1 for checking the syntax error of the created workflow WF, a "Refresh" button SB2 for forcibly refreshing the workflow edit screen W10, a "Save" button SB3 for saving the workflow data D1, D2 in the local disk, and a "Quit" button SB4 for quitting the visual editor 22 are set as functions each of which is executable by the single-click operation of the mouse.

Figure 11:
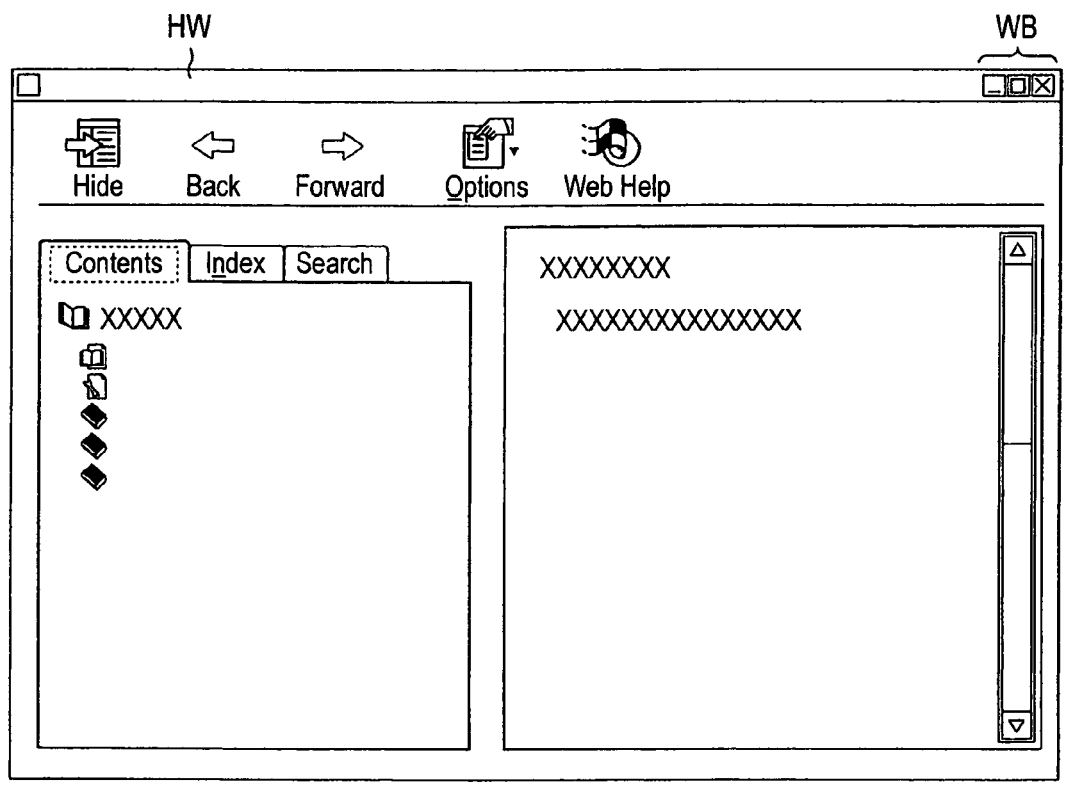
FIG. 11 is a diagram showing a display example of a help screen on the workflow edit screen.

FIG. 11 shows an example of the help screen HW on the workflow edit screen W10. The help screen HW in this example is executed by the wizard function 40, and it is capable of displaying the operating method (explanation of the operations) of the visual editor 22.

3. Workflow Edit Function

Next, the details of the workflow edit function 31 will be described in conjunction with the accompanying drawings.

With the workflow edit function 31, the basic operations of "Menu operations", "Mouse operations" and "Key operations" are supported as user operations. Now, the contents of these basic operations will be described in succession.

(Menu Operations)

Figure 12A:
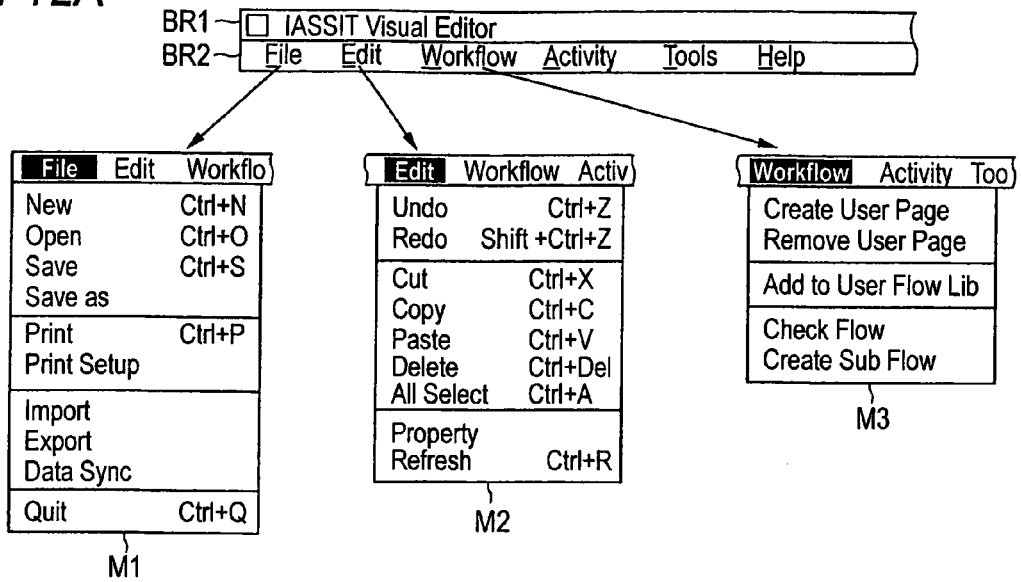

FIGS. 12(a) and (b) show an example of the menu bar BR2 on the workflow edit screen W10. The menu items M1-M6 of "File", "Edit", "Workflow", "Activity", "Tool" and "Help" are set in the menu bar BR2 in this example.

Among them, in the "File" menu M1 shown in FIG. 12(a), there are set the items of "New creation", "Open", "Save", "Save as", "Print", "Print Setup", "Import", "Export", "Data Sync" and "Quit".

Among them, the "New creation" item is selected in creating the new workflow edit screen W10, by the operation of the mouse, the keyboard or the like (including also a key operation "Ct1+N" in the selection of the "File" menu M1). If editing is proceeding on the workflow edit screen W10 in the selection of the "New creation" item, a warning dialog is displayed, and if data being edited exist, whether or not the new workflow edit screen W10 is to be created can be selected after the data being edited have been saved.

Besides, the "Open" item is selected in loading the workflow data D1, D2 saved in the local disk, by the operation of the mouse, the keyboard or the like (including also a key operation "Ct1+O" in the selection of the "File" menu M1). When the "Open" item is selected, a file selecting dialog is displayed, and the load destination of the data can be designated.

Besides, the "Save" item is selected in saving the workflow data D1, D2 in the local disk, by the operation of the mouse, the keyboard or the like (including also a key operation "Ct1+S" in the selection of the "File" menu M1). When the "Save" item is selected, a file selecting dialog is displayed, and a location for the save can be designated.

Besides, the "Save as" item is selected in giving the workflow data D1, D2 another name and saving them in the local disk such as hard disk or MO, by the operation of the mouse, the keyboard or the like. When the "Save as" item is selected, a file selecting dialog is displayed, and a location for the save can be designated.

Besides, the "Print" item is selected in printing the workflow edit screen W10, flow viewer screen W20 or examination status monitor screen W30, by the operation of the mouse, the keyboard or the like (including also a key operation "Ct1+P" in the selection of the "File" menu M1). The print of the workflow edit screen W10 handles only an edit area, and the edit area which is not received within a sheet size can be printed after being divided into a plurality of sheets.

Besides, the "Print setup" item is selected in performing settings relevant to the print, by the operation of the mouse, the keyboard or the like.

Besides, the "Import" item is selected in importing the workflow data D1, D2 created by and exported from the visual editor 22 on another ultrasonic diagnostic equipment 1 or the external PC 3, by the operation of the mouse, the keyboard or the like. The file format of the workflow data D1, D2 on this occasion is, for example, the XML format.

Besides, the "Export" item is selected in exporting the workflow data D1, D2 in order to utilize the data by the visual editor 22 on another ultrasonic diagnostic equipment 1 or the external PC 3, by the operation of the mouse, the keyboard or the like.

Besides, the "Data synchronization" item is executed by the data synchronizing function 38, and it is selected in performing synchronization processing with data managed by the visual editor 22 on another ultrasonic diagnostic equipment 1 or the external PC 3, by the operation of the mouse, the keyboard or the like. This item makes workflow editing possible in the same environment even in a different place. Thus, it is permitted to synchronize the data in the network connection mode or on the basis of the removable medium.

Further, the "Quit" item is selected in quitting the visual editor 22, by the operation of the mouse, the keyboard or the like (including also a key operation "Ct1+Q" in the selection of the "File" menu M1).

In the "Edit" menu M2 shown in FIG. 12(a), there are set the items of "Undo", "Redo", "Cut", "Copy", "Paste", "Delete", "All Select", "Property" and "Refresh".

Among them, the "Undo" item is selected in restoring the last operation for an object, by the operation of the mouse, the keyboard or the like (including also a key operation "Ct1+Z" in the selection of the "Edit" menu M2).

Besides, the "Redo" item is selected in returning into a status before the selection of the "Undo" item after this "Undo" item has been selected, by the operation of the mouse, the keyboard or the like (including also a key operation "Shift+Ct1+Z" in the selection of the "Edit" menu M2) Besides, the "Cut" item is selected in deleting an object, by the operation of the mouse, the keyboard or the like (including also a key operation "Ct1+X" in the selection of the "Edit" menu M2). The object deleted by the selection of the "Cut" item can be made subjects for the undo, redo and copy operations.

Besides, the "Copy" item is selected in copying an object, by the operation of the mouse, the keyboard or the like (including also a key operation "Ct1+C" in the selection of the "Edit" menu M2).

Besides, the "Paste" item is selected in pasting an object, by the operation of the mouse, the keyboard or the like (including also a key operation "Ct1+V" in the selection of the "Edit" menu M2).

Besides, the "Delete" item is selected in deleting an object, by the operation of the mouse, the keyboard or the like (including also a key operation "Ct1+Del" in the selection of the "Edit" menu M2).

Besides, the "All select" item is selected in deleting all objects, by the operation of the mouse, the keyboard or the like (including also a key operation "Ct1+A" in the selection of the "Edit" menu M2).

Besides, the "Property" item is selected in displaying a property such as activity or workflow, by the operation of the mouse, the keyboard or the like.

Further, the "Refresh" item is selected in redepicting the display of the workflow edit screen W10, by the operation of the mouse, the keyboard or the like (including also a key operation "Ct1+R" in the selection of the "Edit" menu).

In the "Workflow" menu M3 shown in FIG. 12(a), there are set the items of "Create User Page" which adds a page into the "User" tab TB11 (refer to FIG. 6) on the workflow library screen W11, "Remove User Page" which removes a page in the same "User" tab TB11, "Add to User Flow Lib" which adds the workflow D1 created by the user, as a template onto a page in the same "User" tab TB11, "Check Flow" which executes the syntax check of the workflow created by the user, "Workflow Attribute" which sets the control attribute of the workflow, and "Create Sub Flow" which alters the icon AP of a selected activity into a subworkflow being at the lower hierarchical level of the workflow WF.

In a case where, during the selection of the "Create Sub Flow" item among the various items, the icon AP being already in the subworkflow has been clicked with the mouse, the name of a displayed item changes from the "Create Sub Flow" into "Release Sub Flow".

Figure 12B:
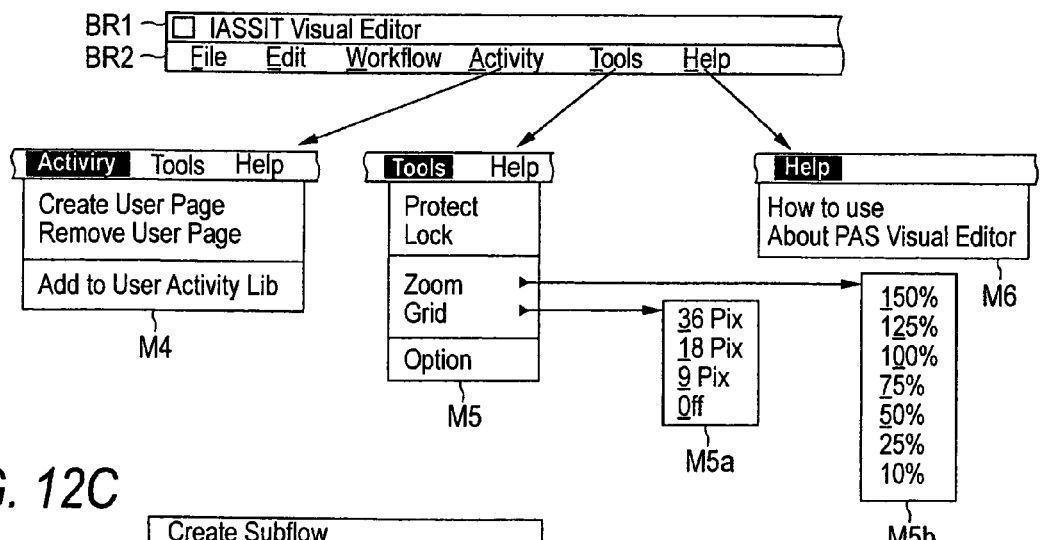

In the "Activity" menu M4 shown in FIG. 12(b), there are set the items of "Create User Page" which adds a page to the "User" tab TB12 (refer to FIG. 7) in the activity library screen W12, "Remove User Page" which removes the page of the same "User" tab TB12, and "Add to User Activity Lib" which adds the activity 23a to the page of the same "User" tab TB12, as the icon AP.

In the "Tool" menu M5 shown in FIG. 12(b), there are respectively set the items of "Protect" which applies protection to an activity or a workflow subjected to user registration in the workflow library screen W12 (in a case where a workflow already protected has been selected, the "Protect" changes over to "Non-protect"), "Lock" which locks the object, such as the icon AP of the activity or the comment, arranged on the workflow design screen W13, so as not to be moved from the arranged place thereof by drag or the like operation (it is also impossible to delete the locked object), "Zoom" which performs the enlarged/reduced display of the workflow design screen W13 (the percentage of the enlargement can be selected on the submenu M5b of the menu M5), "Grid" which sets the grid of the workflow design screen W13 (a grid size can be selected on the submenu M5a of the menu M5), and "Option" which sets any option concerning the visual editor 22.

In the "Help" menu M6 shown in FIG. 12(b), there are set the items of "How to use" which indicates how to use the visual editor 22 in the help form of, for example, Windows standard, and "About PAS Visual Editor" which indicates the version information, etc. of the visual editor 22.

Figure 12C:
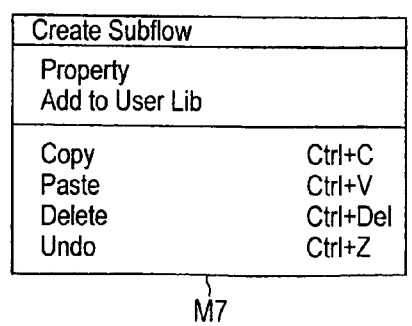
FIG. 12(c) is a diagram showing a display example of a popup menu on the workflow edit screen.

FIG. 12(c) shows an example of the popup menu M7 on the workflow edit screen W10. In the popup menu M7 in this example, the items of "Create Subworkflow", "Property", "Add to User Lib", "Copy", "Paste", "Delete" and "Undo" among the submenu items in the above menu bar BR are alterably registered.

(Mouse Operation)

Next, the mouse operation will be described. Regarding the mouse operations, in case of selecting an activity, a click operation is resorted to; in case of arranging/moving the activity, drag & drop operations are resorted to; in case of creating a subworkflow, a plurality of pertinent activities are selected, and the "Create subworkflow" item (refer to FIG. 12) of the popup menu M7 is selected; in case of releasing a subworkflow, a plurality of pertinent activities in the subworkflow are selected, and the "Release subworkflow" item of the popup menu M7 is selected; and in case of moving a subworkflow, a left double click operation or a right click operation and the selection of the "Open" item of the popup menu M7 are performed.

Here, the "Create subworkflow" item and "Release subworkflow" item of the popup menu M7 are indicated at the same indicating position in the menu while being changed-over. That is, in a case where a selected object has been turned into a subworkflow, the "Release subworkflow" item is indicated, and in a case where an activity not turned into a subworkflow has been selected, the "Create subworkflow" item is indicated.

Besides, in case of selecting a plurality of activities, a "Shift" key operation and a left click operation are resorted to; in case of indicating the property of an activity, a right click operation and the selection of the "Property" item of the popup menu M7 are performed; in case of copying an activity, a right click operation and the selection of the "Copy" item of the popup menu M7 are performed; in case of deleting an activity, a right click operation and the selection of the "Delete" item of the popup menu M7 are performed; in case of pasting an activity, a right click operation and the selection of the "Paste" item of the popup menu M7 are performed; and in case of undoing an activity, a right click operation and the selection of the "Undo" item of the popup menu M7 are performed.

(Key Operation)

Next, there will be described key operations which handle objects such as a user-registered workflow in the workflow library screen W11, a user-registered activity in the activity library screen W12, an activity icon AP arranged on the workflow design screen W13, and a comment described on the workflow design screen W13.

Regarding the key operations, in case of copying an object, the key operation of "Ctrl"+"C" or the key operation of "Ctrl" and the drag operation of the object are resorted to (on this occasion, in a case where a plurality of selected objects are to be handled, they are respectively copied); in case of deleting an object, the key operation of "Ctrl"+"X" or a "Del" key operation in a object selection state is resorted to; in case of pasting an object, the key operation of "Ctrl"+"V" is resorted to; and in case of undoing an object, the key operation of "Ctrl"+"Z" is resorted to.

Next, there will be described workflow editing which is performed on the basis of the above basic operations (menu operation, mouse operation, key operation).

(Addition of New Activity to Activity Library)

As stated before, the activity 23a is created from an ActiveX component by way of example, and it is utilizable in the visual editor 22 and the workflow system 21 of the ultrasonic diagnostic equipment 1. Therefore, the activity 23a can be added anew and deleted on the activity library screen W12 by the foregoing operations.

(Arrangement of Activity Icons)

Owing to the foregoing operations, the user can visually arrange activity icons AP on the workflow design screen W13.

Figure 13:
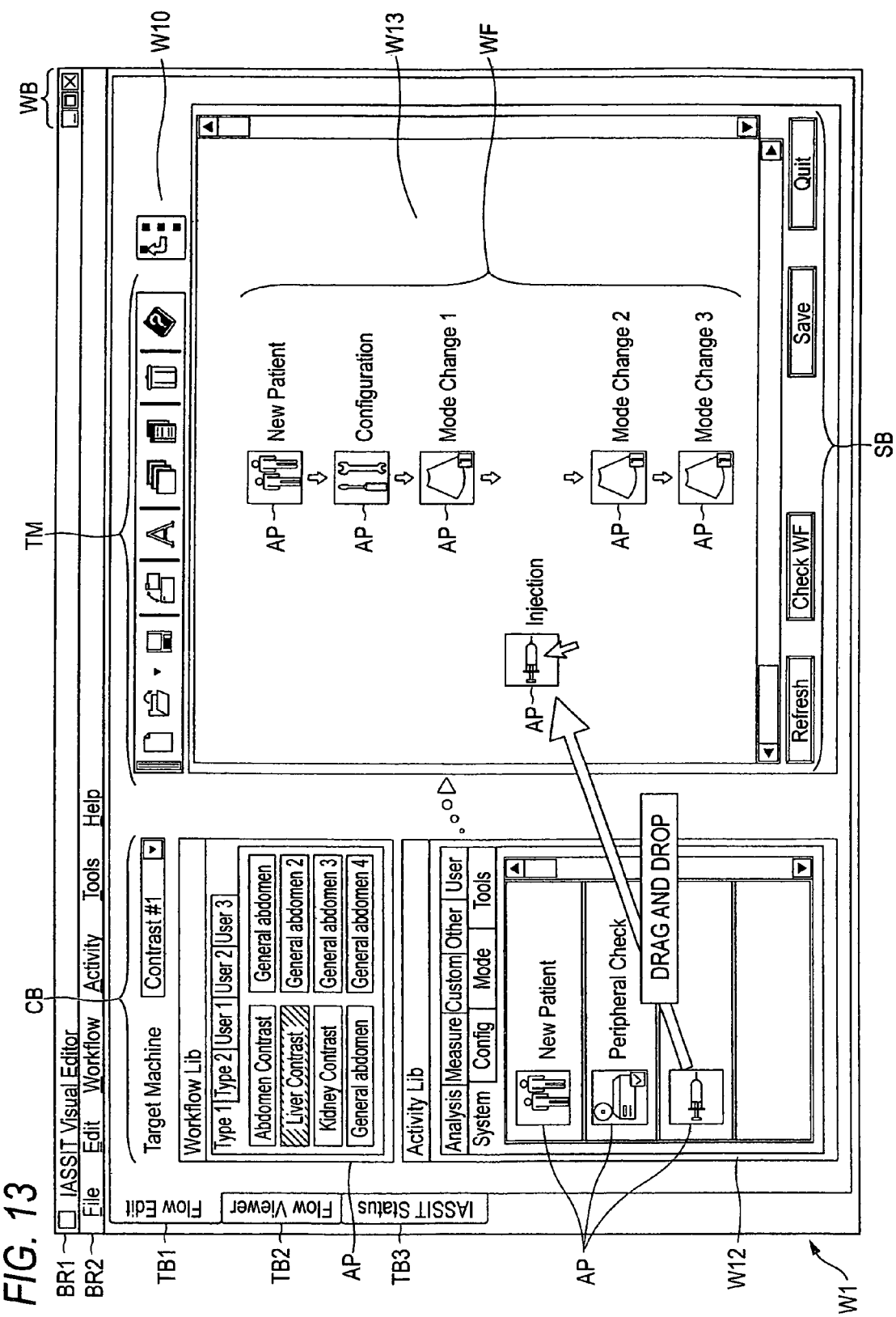
FIG. 13 is a diagram for explaining an activity icon arrangement based on drag & drop operations.

FIG. 13 shows an example of the arrangement of the activity icons AP on the workflow edit screen W10 as based on drag & drop operations. As shown in FIG. 13, the user can arrange the activity icons AP so as to constitute a workflow WF, from the activity library screen W12 onto the workflow design screen W13 through the drag & drop operations of the mouse.

Activity names are displayed as comments on the right sides of the activity icons AP thus arranged. The setting of the display/nondisplay of the comments is performed on a predetermined GUI screen (for example, option dialog editor) which is displayed by selecting the "Option" item in the "Tool" menu M5 on the menu bar BR2.

Figure 14A:
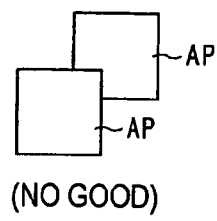
FIGS. 14(a) and (b) are diagrams for explaining the fact that the overlapping arrangement of activity icons is not permissible.
Figure 14B:
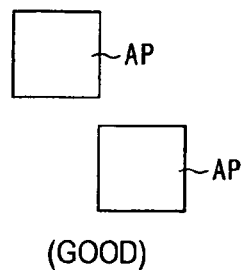

In performing the drag & drop operations to the workflow design screen W13, the icons AP, AP of two activities 23a, 23a cannot be arranged in overlapping fashion as shown in FIG. 14(a), and they need to be arranged apart as shown in FIG. 14(b).

Besides, on the workflow design screen W13, the order of execution of the workflow WF in the workflow system 21 conforms basically to the arrangement order of the activities on the screen W1 (the workflow is sequentially executed from the upper side of the screen toward the lower side thereof).

Figure 15:
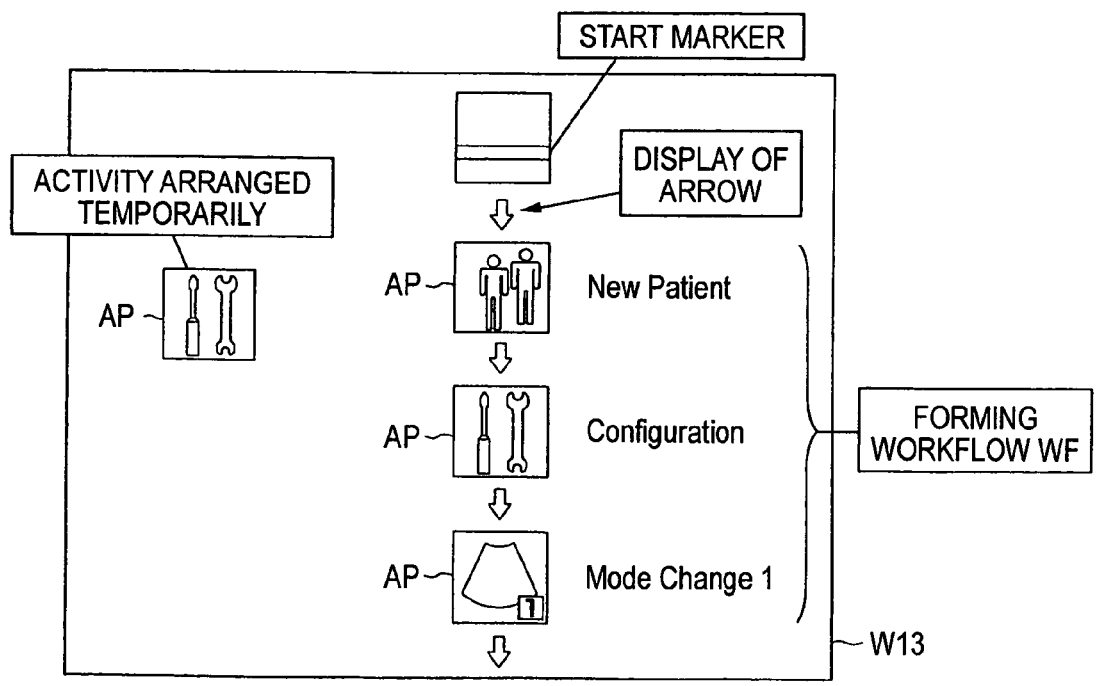
FIG. 15 is a diagram for explaining the first stage of workflow description based on activity icons.

As shown in FIG. 15, the workflow WF which is edited on the workflow design screen W13 is headed by a start marker located on the upper side of the screen and is arranged and formed underneath the start marker. Herein, when the first activity icon AP has been arranged underneath the start marker by a drag operation, an arrow mark which couples the activity icon and the start marker is automatically displayed as shown in FIG. 15. On this occasion, the activity icon AP can be arranged in any place which does not lie underneath the start marker. In this case, the visual editor 22 recognizes the arrangement of the activity icon AP as a temporary one as shown in FIG. 15 (that is, the activity 23a corresponding to the icon is not the constituent of the workflow WS).

Figure 16:
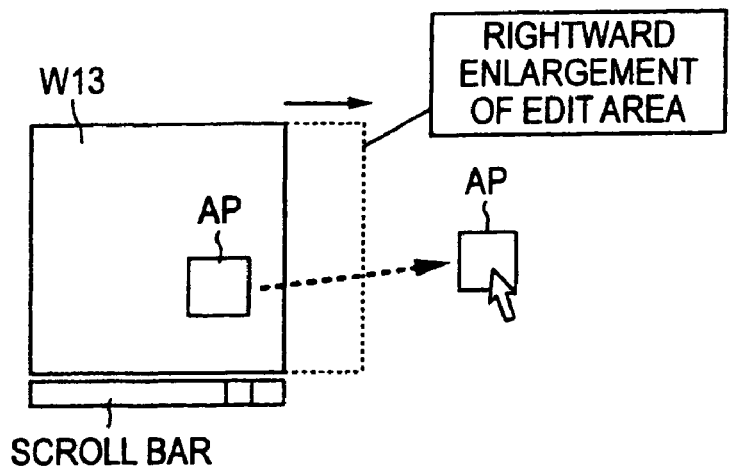
FIG. 16 is a diagram for explaining the fact that an edit area is enlarged with the movement of an activity icon.

Besides, the workflow design screen W13 is furnished with horizontal and vertical scroll functions. In a case where, as shown in FIG. 16 by way of example, the user has moved the activity icon AP to a position outside the display area of the edit area on the screen W1 while dragging this icon (in the illustrated example, the user has moved the icon rightwards), the edit area is automatically enlarged in conformity with the movement. The enlarging direction of the edit area on this occasion agrees with the drag direction of the icon AP, and it becomes rightward in the example of FIG. 15. Since the display area of the workflow design screen W13 has a fixed size, a scroll bar is displayed in the case of the enlargement of the edit area, and the display area is virtually enlarged.

(Selection of Activity)

Figure 17:
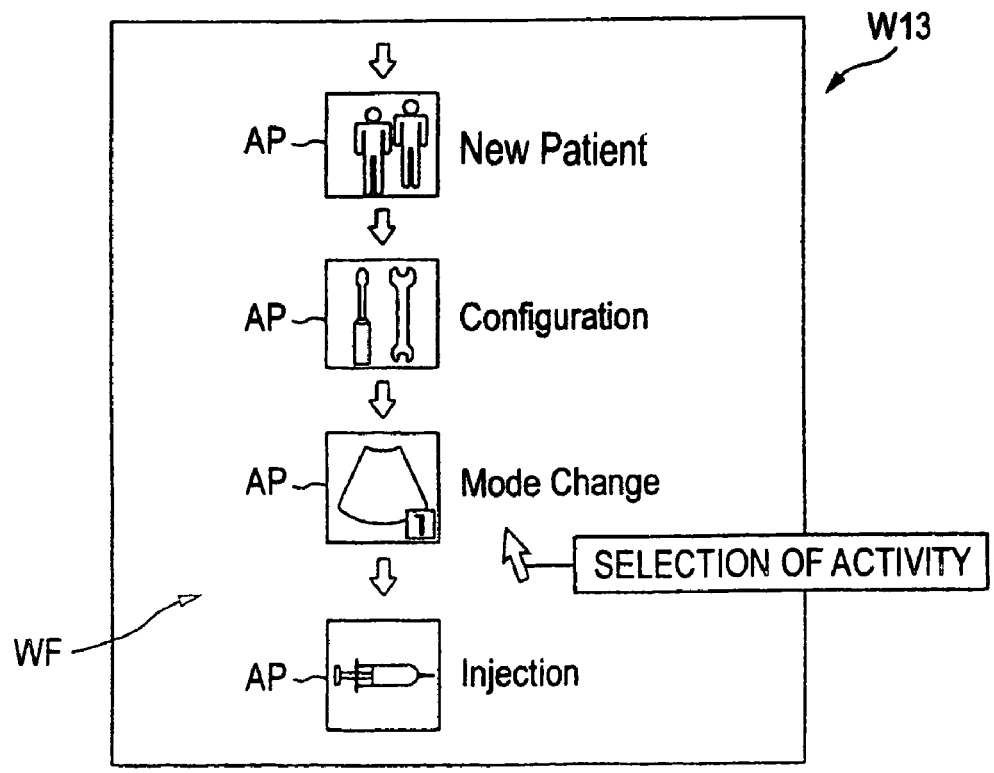
FIG. 17 is a diagram for explaining the selection of an activity icon.

FIG. 17 shows an example of the selection of the activities 13a. When a certain one of the activity icons AP arranged on the workflow design screen W13 is clicked with the mouse as shown in FIG. 17, the icon falls into a selected state, and when it is clicked again, it has its selection released. In this case, a plurality of activity icons AP are selected by a "Ctrl" key operation and a click operation. The surrounding frame (of, for example, 1 [pix (pixel)]) of the selected icon AP is displayed in, for example, a cyan color (of, for example, R:51, G:255 and B:255), so that the selected icon is easily distinguished from the other unselected icons AP.

A plurality of activity icons AP-AP can be selected at one time by the above mouse drag operation. In this case, when one activity icon AP is clicked after the selection of the plurality of icons, only this icon AP falls into the selected state, and the selected states of the other activity icons AP are released. Besides, when a part other than the activity icons AP on the screen W13 is clicked after the selection of the plurality of icons, all the activity icons AP-AP fall into released states.

(Movement of Activity)

An activity 23a is moved by the above mouse drag operation. In case of dragging the mouse in a state where a plurality of activity icons AP have been selected, all the activity icons AP are simultaneously moved.

(Delete, Copy, Paste, Undo and Redo of Activity)

The activity icon AP is deleted by selecting the "Delete" item on the "Activity" menu M4 within the menu bar BR2 stated before. Besides, the activity icon AP is copied by the selection of the "Copy" item on the same "Activity" menu M4. Further, the activity icon AP is pasted into a place on the screen as last clicked with the mouse, by selecting the "Paste" item on the same "Activity" menu M4. The "undo" of the activity icon AP is possible only once after "delete", "copy", "paste" and "move", and "redo" is permitted for this "undo". The above functions are possible, not only by mouse operations, but also by the menu operations stated before.

Figure 18:
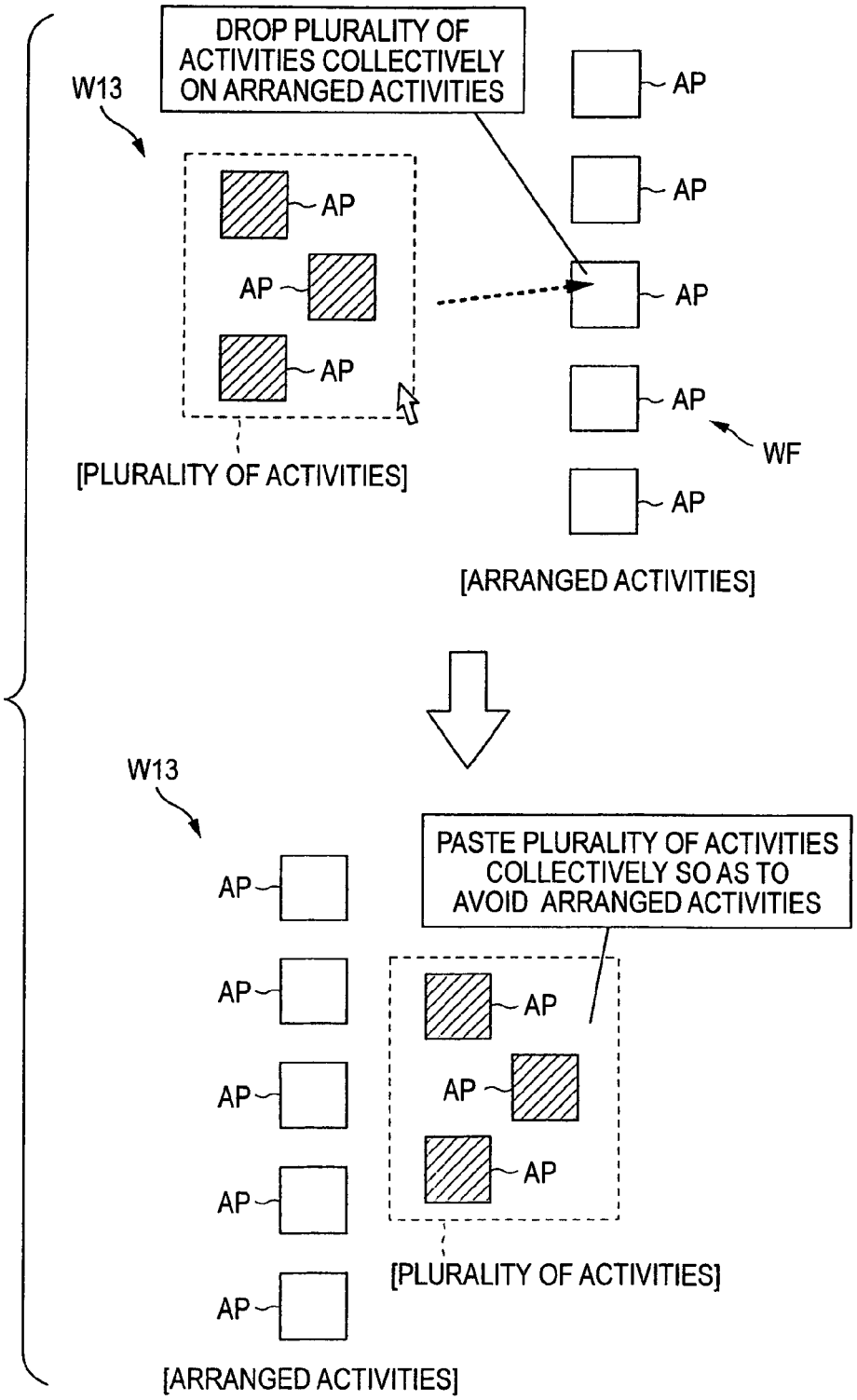
FIG. 18 is a diagram for explaining a case where a plurality of activity icons are collectively pasted.

FIG. 18 shows an example in the case of pasting a plurality of activities 23a-23a collectively. In this example, the plurality of activities 23a are collectively pasted onto the workflow design screen W13 by the drag & drop operations of the mouse. In this case, if any activity icon AP already arranged exists on the workflow design screen W13, the plurality of activity icons AP-AP are pasted so as to avoid the position of the arranged icon AP.

(Array and Arrangement fixation of Activities)

The plurality of activity icons AP-AP arranged on the workflow design screen W13 by the above operations are arrayed at aligned positions by employing a known arraying method, for example, an arraying function installed in the word processor software "MS-Word" of Microsoft Corporation in U.S.

Besides, the activity icon AP or characters arranged on the workflow design screen W13 has/have its/their position fixed in such a way, for example, that the user selects the object and thereafter selects the "Lock" item in the "Tool" menu M5 on the menu bar BR2. The object thus arranged and fixed is unlocked by selecting the "Unlock" item of the same "Tool" menu M5. In a state where an object already arranged and fixed has been selected, the "Lock" item of the same "Tool" menu M5 is automatically altered to the "Unlock" item. The fixation of the arrangement is released by the selection of the "Unlock" item.

(Grid Arrangement of Activities)

Figure 19:
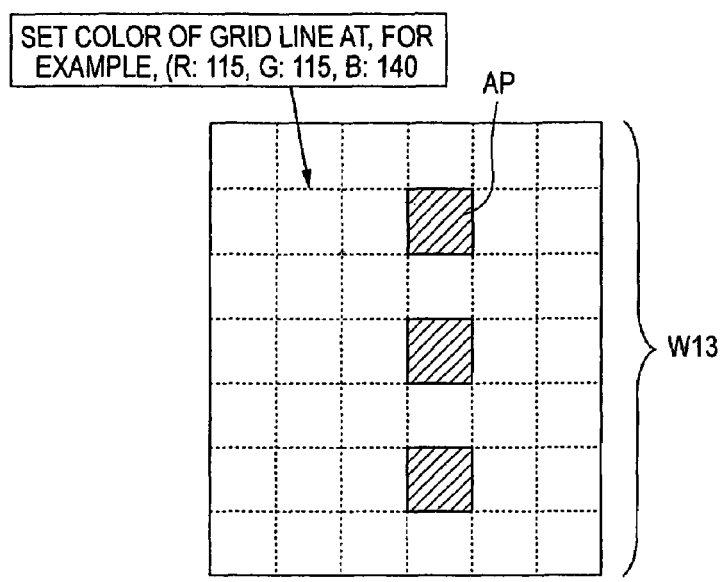
FIG. 19 is a diagram for explaining the grid arrangement of activity icons.

FIG. 19 shows an example of the grid arrangement of activity icons AP. As shown in this example, the grid arrangement in the workflow design screen W13 is turned ON/OFF by, for example, the selection of the "Grid" item within the "Tool" menu M5 on the menu bar BR2. Besides, a grid size is set by designating, for example, 1*1 [pix (pixel)] when the grid arrangement is OFF, and for example, any of 9*9, 18*18 and 36*36 [pix] when the grid arrangement is ON, on the submenu M5a (refer to FIG. 12(b)) displayed by the selection of the "Grid" item stated before. As shown in FIG. 19, the activity icons AP are arranged in conformity with the grid size.

Grid lines which are displayed on the workflow design screen W13 by the above operations, can also be displayed by broken lines. The display/nondisplay of the grid lines is set on a predetermined GUI screen (for example, option dialog editor) which is displayed by the selection of the "Option" item of the "Tool" menu M5 on the menu bar BR2. The color of the grid lines is displayed under the color conditions of, for example, R:51, G:255 and B:255.

(Enlargement or Reduction of Edit Area)

The display enlargement percentage of the edit area can be set on the workflow design screen W13. The display enlargement percentage is set by designating any of, for example, 150%, 125%, 100%, 75%, 50%, 25% and 10% on the submenu M5b (refer to FIG. 12(b)) which is displayed by the selection of the "Zoom" item of the "Tool" menu M5.

(Associated Activity Displaying Function)

Figure 20:
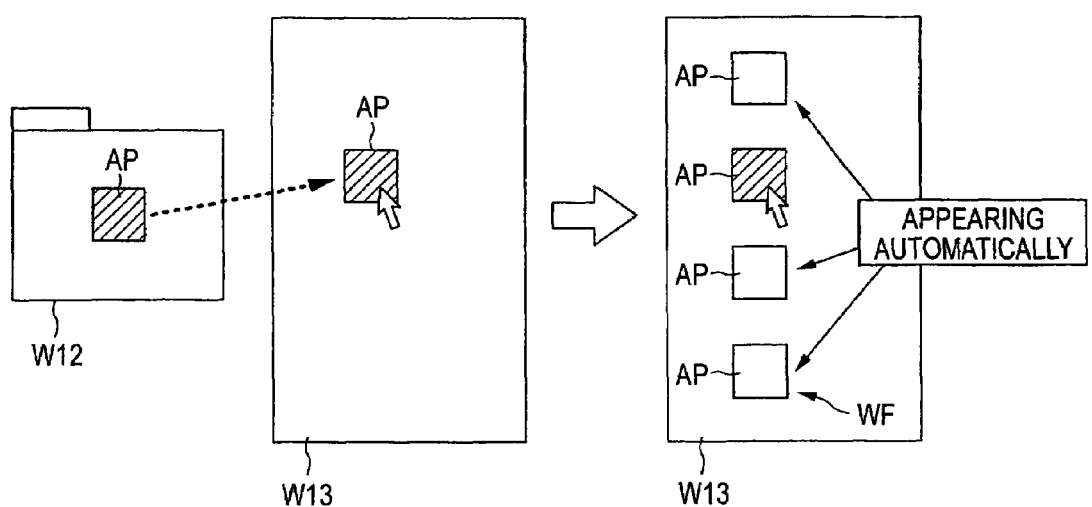
FIG. 20 is a diagram for explaining the movements and automatic appearance of a plurality of associated activity icons.

FIG. 20 is for explaining an associated activity displaying function. With the function, activities 23a which do not operate by themselves, and other activities 23a which operate by themselves, are associated and registered through identification information (such as group identifying ID) beforehand. Thus, in a case where, when a certain activity icon AP has been moved from on the activity library screen W12 and arranged on the workflow design screen W13 as shown in FIG. 20, other activities 23a having, for example, the same group ID are existent, they are automatically arranged collectively. The icons AP on this occasion are automatically arranged from the upper side to the lower side in accordance with the condition of, for example, an arrangement order previously set (designated).

(Description of Workflow)

Figure 21:
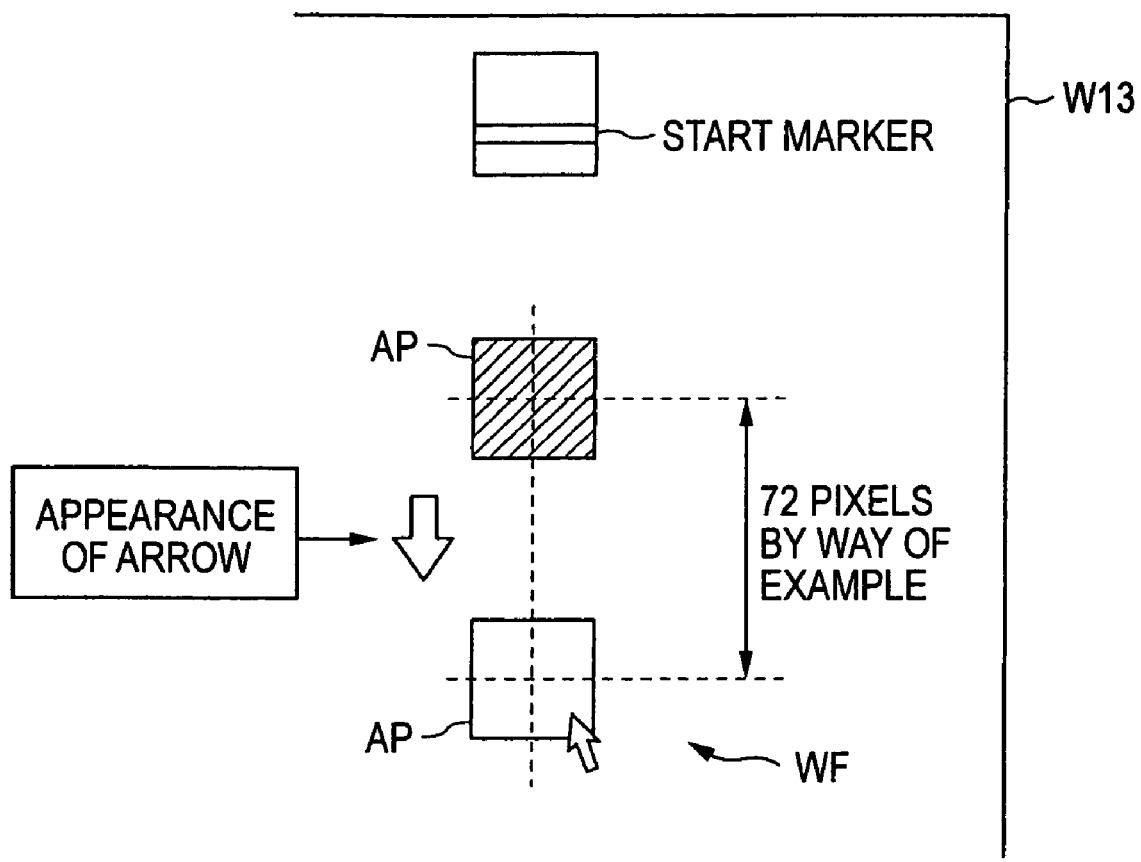
FIG. 21 is a diagram for explaining flow description on a workflow design screen.

FIG. 21 is for explaining flow description on the workflow design screen W13. The sequence of the workflow WF corresponds to the order of execution which proceeds from the upper side to the lower side on the workflow design screen W13 as shown in FIG. 21, and activity icons AP are arrayed in this order. The description of the workflow WF is started from the start (description) marker stated before.

As shown in FIG. 21, an arrow which indicates connection is displayed between the icons AP, AP of two activities 23a, 23a which are vertically adjacent on the workflow WF. The arrow automatically appears in a case where the center distance between the icons AP, AP of the two activities 23a, 23a has approached a reference value, for example, at most 72 [pix (pixels)]. In this case, even if the activity is being dragged with the mouse, the arrow automatically appears in the case where the distance has approached, at most, the reference value.

Figure 22:
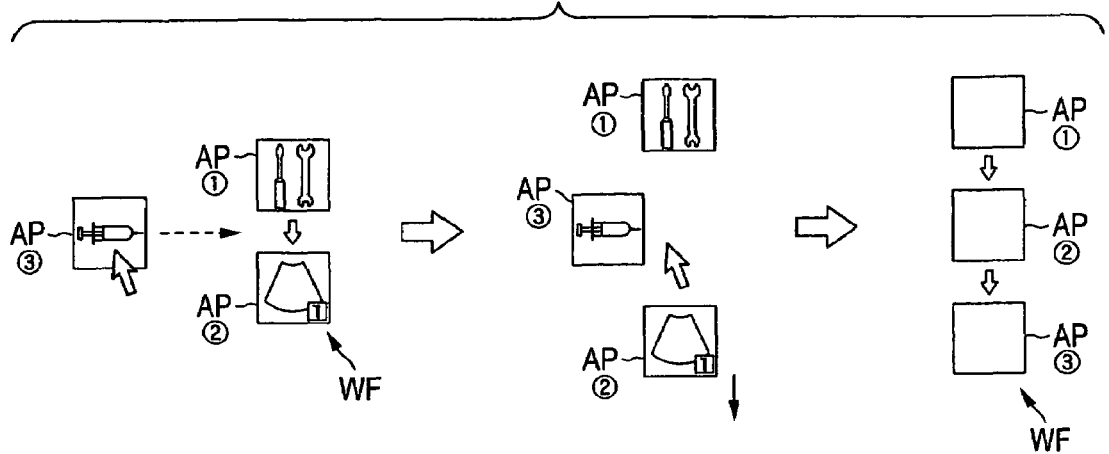
FIG. 22 is a diagram for explaining the movement of an activity icon into a workflow and the automatic enlargement of the interspace between icons.

As shown in FIG. 22, in a case where another activity icon AP(3) has been dragged between the icons AP(1), AP(2) of the two activities 23a, 23a which are vertically adjacent to each other on the workflow WF, the interspace between the two vertical icons AP(1), AP(2) on the workflow WF is automatically expanded (the upper AP(1) is fixed as it is, and the lower AP(2) is moved onto the lower side still further), so that the other icon AP(3) is permitted to be inserted. After the insertion of the other icon AP(3), arrows automatically appear to be displayed between the icons AP(1) and AP(3) and between the icons AP(3) and AP(2).

Figure 23:
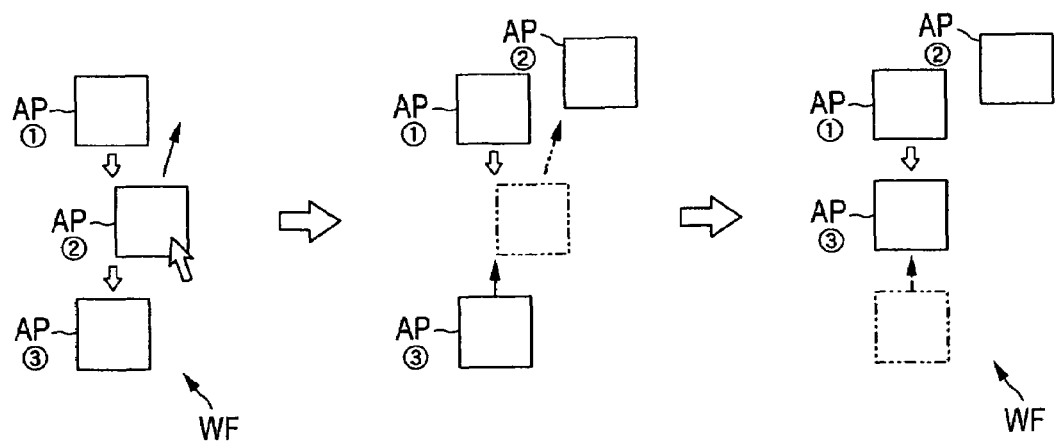
FIG. 23 is a diagram for explaining the movement of an activity icon from a workflow and the automatic reduction of the interspace between icons.

As shown in FIG. 23, in a case where the middle one AP(2) of the three activity icons AP(1), AP(2), AP(3) which are vertically adjacent to one another on the workflow WF has been moved, the interspace between the two remaining activity icons AP(1), AP(3) is automatically reduced so as to fill the resulting vacancy (the directly overlying AP(1) is fixed as it is, and the directly underlying AP(2) moves upwards), and the icons AP(1) and AP(3) are connected anew.

(Hierarchical Description Including Subworkflow)

As stated before, in the workflow system 21, the flow of a series of jobs configured of a plurality of activities 23a (icons AP) is a workflow WF, which can be hierarchized to lower levels. Here in this specification, the workflows WF of the lower levels thus hierarchized shall be called "subworkflows", while the original workflow WF of the high level shall be called the "main workflow", and both the workflows will be distinguished in the description as may be needed.

With the visual editor 22 described before, the "subworkflows" of, for example, at least 32 hierarchical levels can be described by two sorts of methods explained below.

Figure 24:
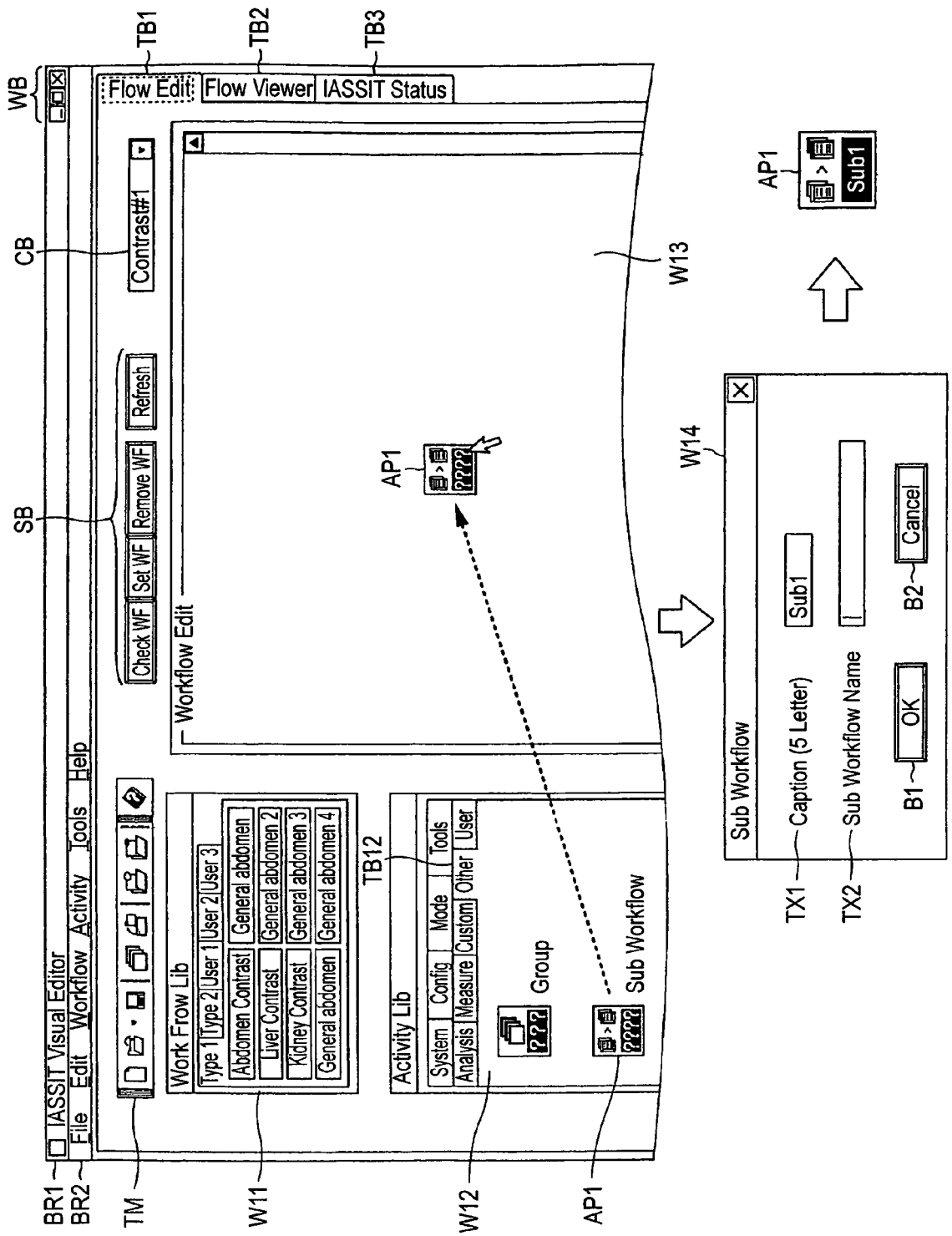
FIG. 24 is a diagram for explaining a method (first method) of describing a subworkflow.

FIG. 24 is for explaining the first method, and the icon of the "subworkflow" (hereinbelow, termed "subworkflow icon") AP1 is initially arranged. In this method, the subworkflow icon AP1 which is set as manufacturer default on the page of the "Other" tab TB12 on the activity library screen W12 is first selected by a user operation, and it is moved from the page and arranged on the workflow design screen W13 by drag & drop operations.

Then, as shown in FIG. 24, a predetermined dialog box W14 is automatically popup-displayed on the screen. The dialog box W14 is for setting the name of the subworkflow, and a text input box TX1 for inputting the caption (of at most 5 letters) of the name, a text input box TX2 for inputting the formal name, an OK button, and a cancel button are respectively laid out at appropriate positions.

The user inputs the subworkflow name on the dialog box W14, and mentioned in the example in FIG. 24 is, for example, a case where the letters of "Sub1" have been inputted into the box TX1 for inputting the caption of the subworkflow name. Thereafter, when the OK button is pressed to close the dialog box W14, the caption "Sub1" of the subworkflow name inputted into the box TX1 is unitarily buried in the lower side of the icon AP1 on the workflow design screen W13 and is displayed as shown in FIG. 24.

In creating the above subworkflow, the user can set the attributes (display attribute and execution attribute) of the subworkflow. The operation of the setting is possible by selecting the "Property" item of the menu BR1 in the selected state of the subworkflow icon AP1, or by selecting the "Property" item of the popup menu displayed by the right click operation of the mouse.

That display attribute of the subworkflow which is set here, concerns the method of displaying the subworkflow on the GUI screen of the ultrasonic diagnostic equipment 1 (host system), and it includes, for example, a "screen changeover display type attribute" and a "selected screen type attribute".

Besides, the execution attribute of the subworkflow concerns the method of returning from the subworkflow to the main workflow through the GUI of the host system, and it includes, for example, an "attribute by which the subworkflow can return to the main workflow in a case where any activity 23a within the subworkflow has been executed" and an "attribute by which the execution of the subworkflow continues until an "EXIT" button displayed in the subworkflow is pressed".

When the subworkflow icon AP1 is double-clicked, screen changeover is effected from the workflow design screen W13 to a subworkflow design screen for describing a subworkflow.

Figure 25:
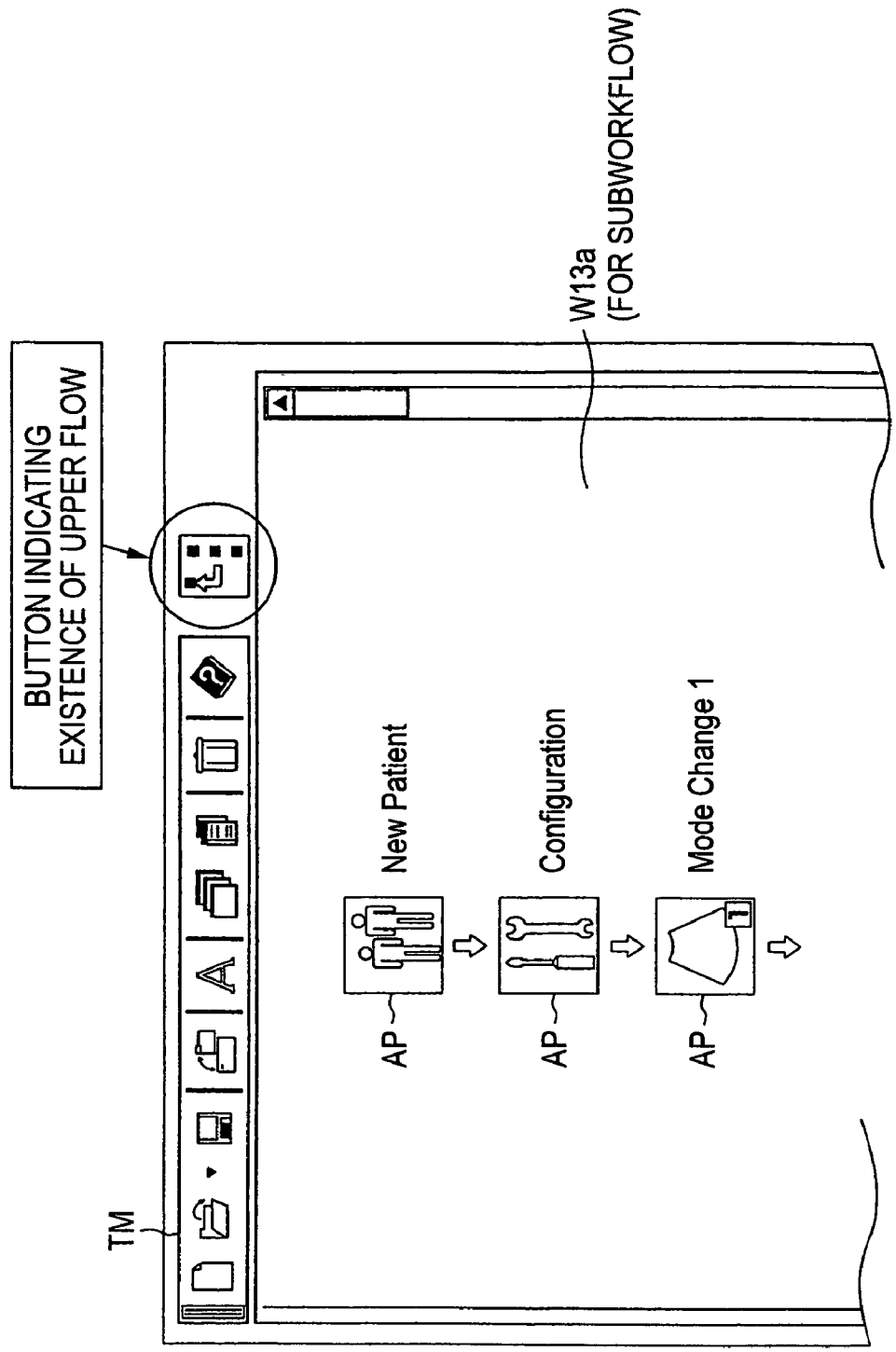
FIG. 25 is a diagram showing a display example of a subworkflow design screen.

FIG. 25 shows an example of the subworkflow design screen W13a. On the subworkflow design screen W13a, the user can create the subworkflow by the same operations as those of the above workflow creation. In a case where the workflow design screen has changed-over to the subworkflow design screen W13a, a peculiar button, which serves to indicate that the workflow WF at the higher level of workflow hierarchy exists, is displayed at an appropriate position (in the illustrated example, the upper side of the design screen W13a) as shown in FIG. 25. The user can change-over the screen to the upper hierarchical level by clicking the button.

Figure 26:
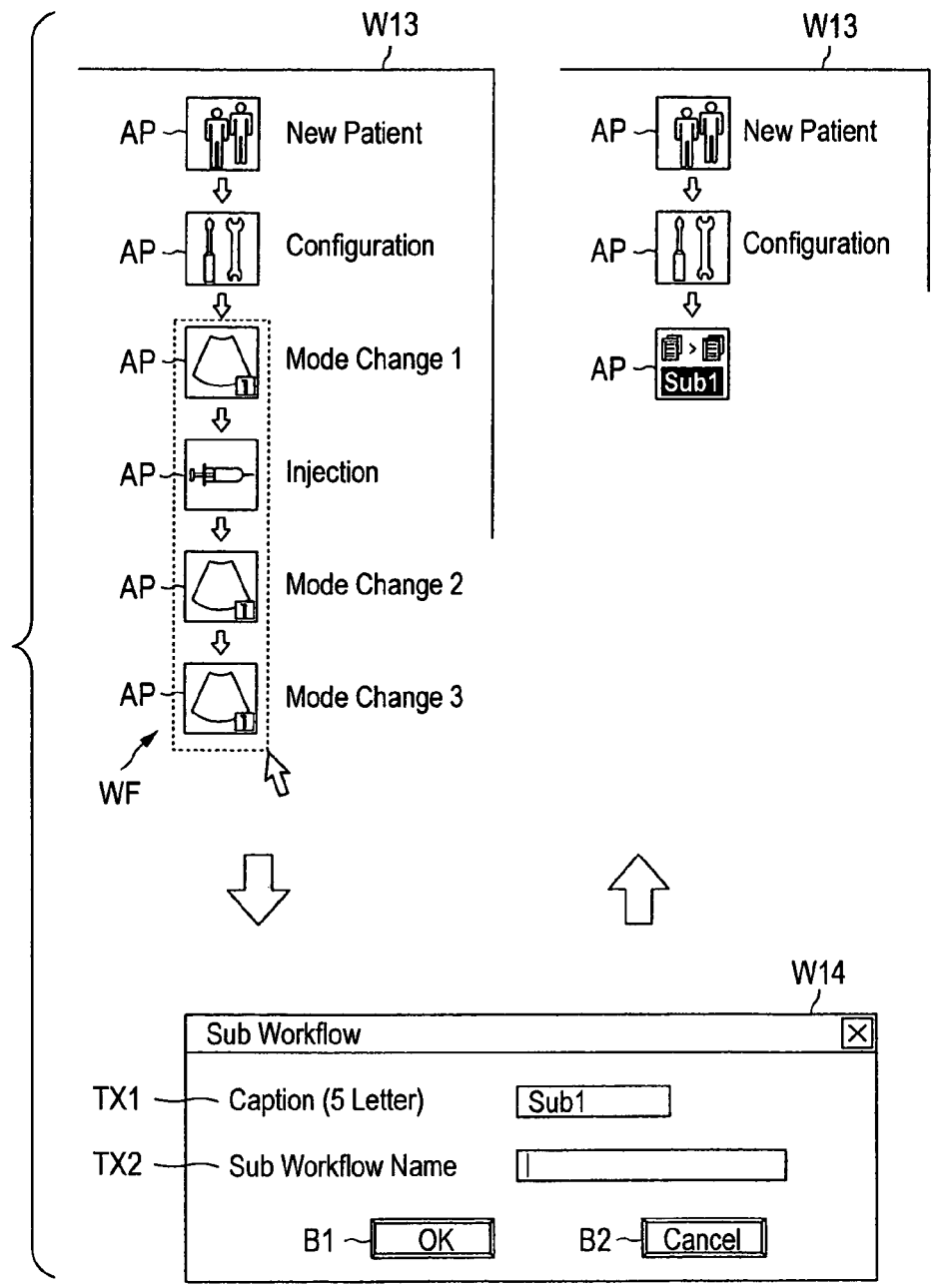
FIG. 26 is a diagram for explaining a method (second method) of describing a subworkflow.

FIG. 26 is for explaining the second method of describing the workflow stated before, and after a plurality of activities 23a have been initially selected, the subworkflow is established. In this method, first of all, activity icons AP-AP being subjects for the subworkflow are selected from among a plurality of activity icons AP-AP constituting the workflow WF and arranged on the workflow design screen W13, as shown in the figure by the operations of the user.

Subsequently, the "Create subflow" item in the "Workflow" menu M3 of the menu bar BR2, or the "Create subflow" item in the popup menu M7 is selected and executed, whereby the same dialog box W14 as in the foregoing is displayed. A subworkflow name (in the illustrated example, the same "Sub1" as in the foregoing) is inputted here, whereby the activity icons AP-AP being the subjects for the subworkflow are changed-over to the subworkflow icon AP1 of the inputted name (in the illustrated example, "Sub1") on the workflow design screen W13.

Figure 27:
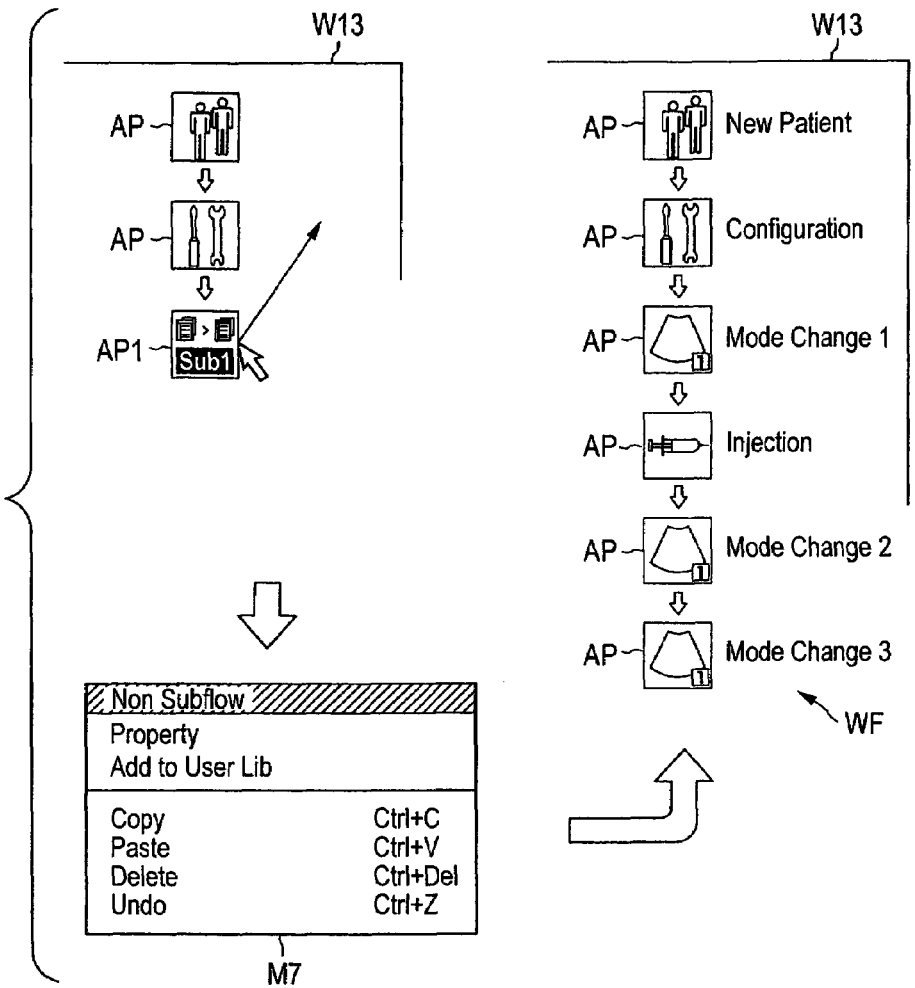
FIG. 27 is a diagram for explaining a method of expanding a subworkflow into a main workflow.

FIG. 27 is for explaining the method of expanding the subworkflow created by either of the two sorts of methods, into the main workflow. According to this method, as shown in the figure, the subworkflow icon AP1 stated before is selected, and the "Release subflow" item in the popup menu M7 displayed by the right click operation of the mouse is selected and executed, through the operations of the user, whereby the subworkflow is released, and the subworkflow icon AP1 is changed-over to a plurality of activity icons AP-AP forming the main workflow at the hierarchically upper level.

(Associating Data Inputs/Outputs Between Activities)

Figure 28:
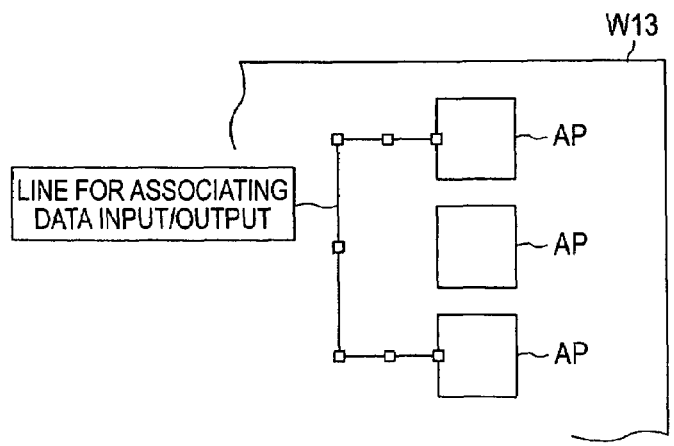
FIG. 28 is a diagram for explaining a method of associating data inputs/outputs among a plurality of activities.
Figure 29:
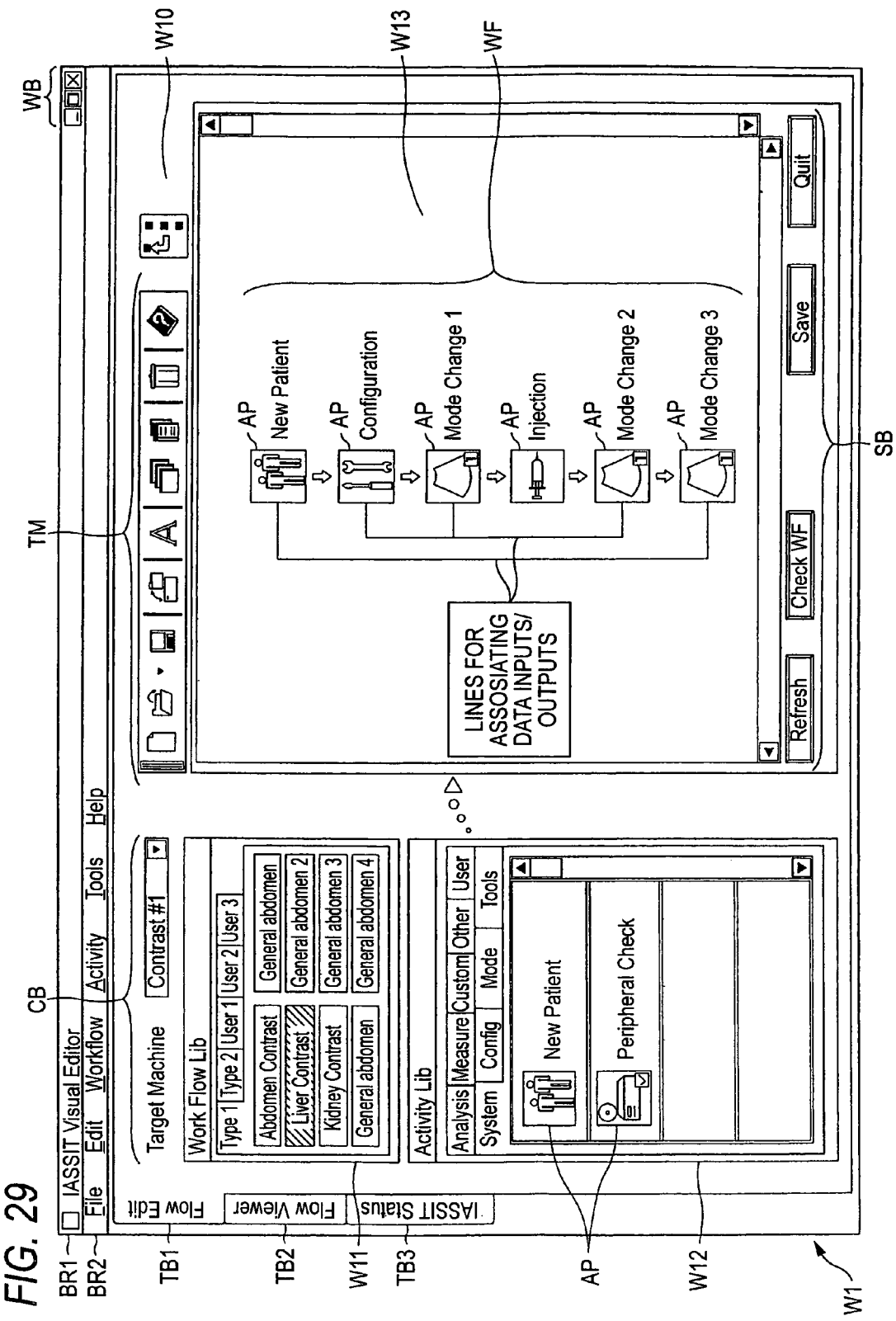
FIG. 29 is a diagram for explaining a display example of a workflow which is formed of a plurality of activities associated in FIG. 28.

FIGS. 28 and 29 are for explaining a case where data inputs/outputs are associated among a plurality of activities 23a, 23a. The data input/output can be associated between the activities 23a each of which has the input/output I/F (interface) of data. The operation of the association can be performed by coupling the activity icons AP, AP being subjects for the association, with a predetermined line as shown in the figures (by way of example, only the activities 23a whose I/F types in ActiveX match can be connected).

An example of operating steps for the association will be described. 1) A "Connect data" item (not shown) in the "Activity" menu M4 on the menu bar BR2 is selected and executed, 2) the mode of the mouse operation is changed-over into a mode permitting the association, 3) a line is drawn between the activity icons AP, AP being subjects for the association by a mouse operation (by way of example, the line is drawn by the operation of "click+drag", and it is deleted by the operation of "click+"Del" key", and 4) the activities 23a, 23a whose input/output types match are connected by coupling the activity icons AP, AP with a line.

By the way, in the case where the I/F types match, the plurality of activities can be connected. In a case where the line has been clicked and selected, square selection markers are displayed on the selected line, and the line is automatically bent and shaped, as shown in FIG. 28. The line can also be moved (extended) by dragging the mouse. The color of the line is, for example, yellow (R:255, G:255, B:0), and the line can be drawn at a line width of 1 [pix] and a grid interval of 9 [pix].

(Description of Conditional Branch and Iteration (Loop) of Workflow)

Figure 30:
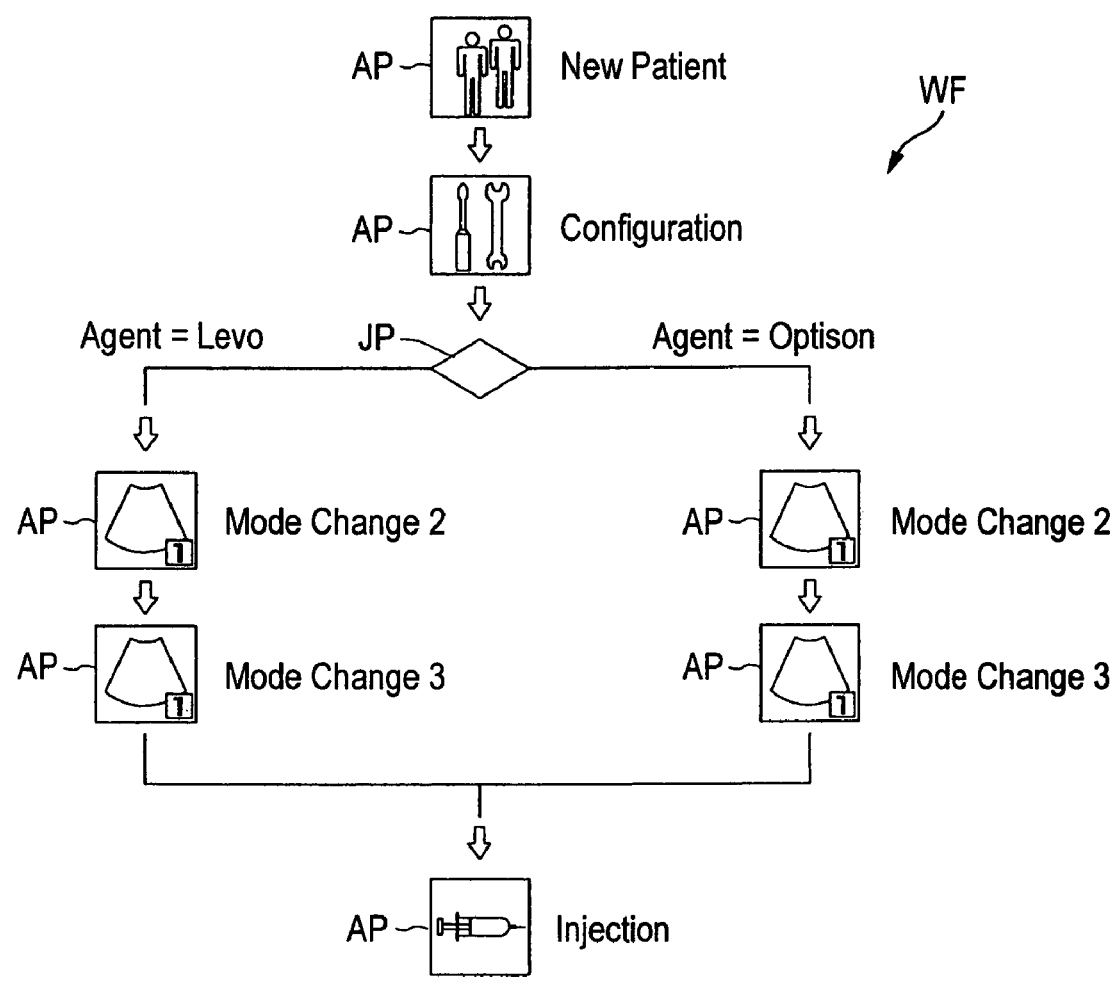
FIG. 30 is a diagram for explaining the conditional branch of a workflow.

FIG. 30 shows an example of the conditional branch of the workflow WF. As shown in FIG. 30, a processing step JP for the conditional branch, by which the workflow WF is branched and shifted to a different routine in accordance with a preset condition just as in a flow chart, can be set by user operations at a predetermined position on the workflow WF which is described by a plurality of activity icons AP-AP. In this example, the condition of the conditional branch is so set that difference examination sequences can be executed depending, for example, upon whether the sort of an ultrasonic contrast agent is Levovist or Optison.

Figure 31:
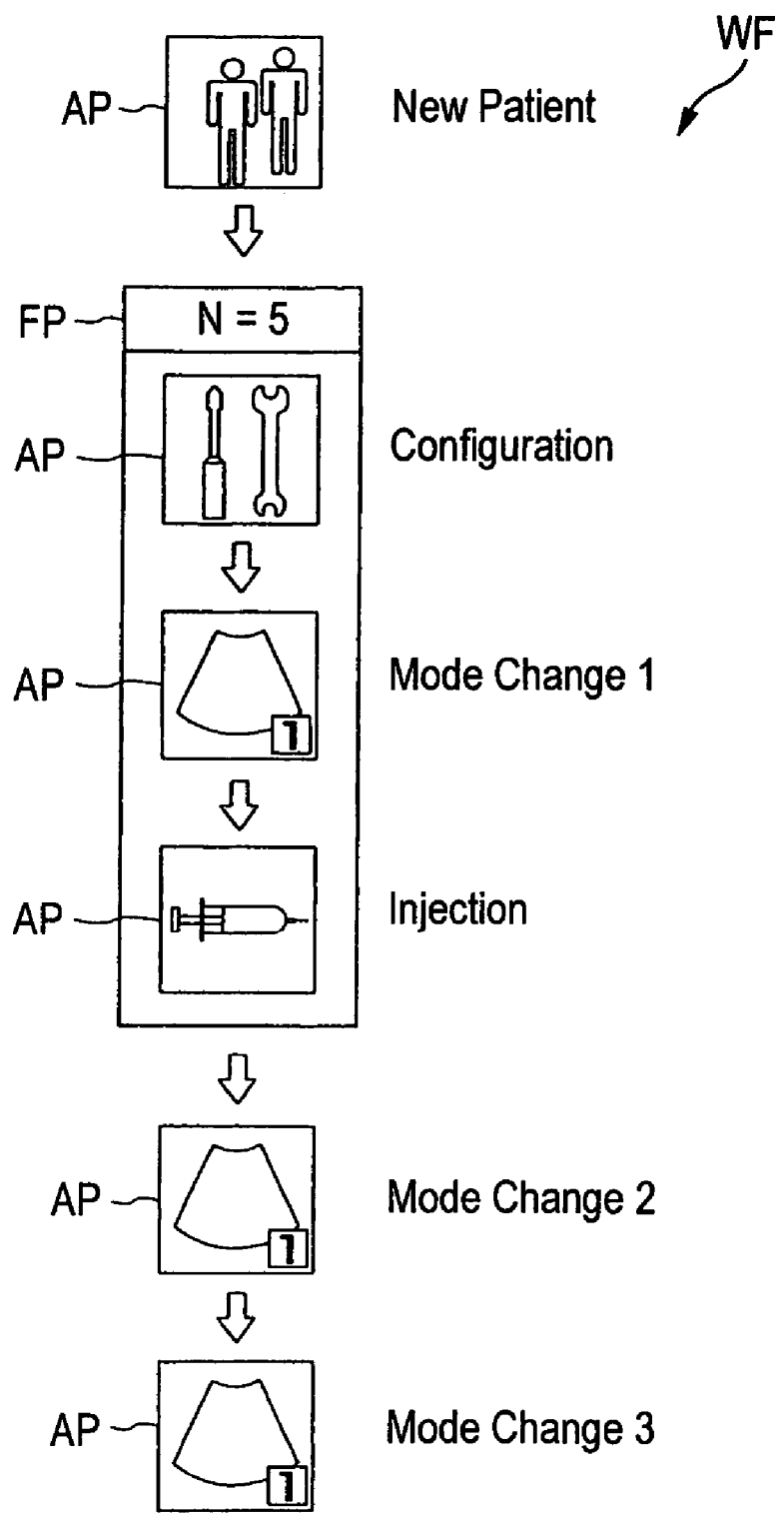
FIG. 31 is a diagram for explaining the iteration processing of a workflow.

FIG. 31 shows an example of the iteration (loop) of the workflow WF. As shown in FIG. 31, a processing step FP for executing a plurality of activity icons AP-AP iteratively a predetermined number of times can be set by user operations in the workflow WF which is described by a plurality of activity icons AP-AP. In this example, the processing step FP which is to iteratively process three activity icons AP-AP is set, and the number of times of iteration, N=5 is displayed in the processing step FP. The processing steps of activities 23a-23a corresponding to the three activity icons AP-AP are iteratively executed the number of times.

(Setting of Execution attribute of Activity)

With the visual editor 22 stated before, an execution attribute in the case of executing an activity 23a can be set. The execution attribute can also be set on the GUI screen of the workflow system 21. The information of the attribute to be set here is represented as the TAG of an XML file. The method of the representation is preset by, for example, XML specifications for the workflow system.

FIG. 32 shows a setting example of the execution attribute of the activity. The execution attribute of the activity in this example includes, for example, "Automatic execution", "Manual execution", "Skip" and "Conditional execution". The setting example of each individual execution attribute is as indicated in the figure. In case of the "Automatic execution", "in the workflow system operation, the activity is automatically executed without waiting a user action"; in case of the "Manual execution", "in the workflow system operation, a user action is waited, and the activity is executed upon the action"; in case of the "Skip", "the activity is not executed in the workflow system operation, and the workflow system executes the next activity"; and in case of the "Conditional execution", "the activity can be executed, or skipped or jumped in accordance with an execution status which the activity replies in the workflow system operation".

(Setting of Attributes of Individual Activity)

With the visual editor 22 stated before, attributes which each individual activity 23a has can be set. An example of the setting is shown in FIG. 33.

As shown in FIG. 33, the dialog box W15 of a GUI attribute menu which the activity 23a has is popup-displayed by the double click of the activity icon AP arranged on the workflow design screen W13, or by the selection of the "Property" item on the popup menu M7 or on the menu bar BR2. The dialog box W15 shown in FIG. 33 is a timer attribute setting menu which concerns the double-clicked activity 23a to-be-handled.

(Entry of Comment)

With the visual editor 22 stated before, a comment can be entered on the workflow design screen W13. When Comment is double-clicked with the mouse, dialogs (not shown) for altering font attributes are displayed, and a color, a font size and a format can be altered in accordance with the dialogs. Initial values are set at, for example, Arial, 12 points, etc. A plurality of comments can be entered onto the workflow design screen W13, they can be moved by drag operations, and they can be revised. The operation of a character editing mode for entering the comment can be performed by, for example, mouse click operation+fast mouse cursor movement.

(Registration History Log)

With the visual editor 22 stated before, it is possible to retain history information in the case where registration, deletion or synchronization has been performed. The history information includes, for example, "Date, time and name of workflow editing (addition, deletion or revision)", "Date, time and addition name of addition (user registration) to activity library", "Date, time and addition flow name of addition (user registration) to workflow library", and "Date, time, synchro mode and pertinent device name of synchronization".

Besides, the registration history log can be confirmed on the examination status screen W30. The user cannot alter the registration history log. The registration history log is saved in the text format (in a case where an OS is the Windows type by way of example, only service engineers may be able to refer to the file through a Windows application such as text editor). The maximum file size in which the registration history log is recordable, can be set. The setting is described in, for example, a "VE. ini" file. A default value is set at, for example, 5MB, and in a case where the maximum value has been exceeded, the log is deleted, and a file is created anew.

Besides, it can be set to protect a workflow and an activity 23a which have been user-registered in the ultrasonic diagnostic equipment 1. Once the workflow and the activity have been protected, they cannot be deleted from the workflow library and the activity library, respectively, until the protection is released.

The operation of the protection is performed by bringing the object to-be-protected into a selected state and executing "Protect" on the menu. In a state where an object already protected has been selected, the display of the "Protect" item on the menu is automatically altered to a "Release protect" item. The protection is released by selecting the "Release protect" item.

Besides, with the visual editor 22 stated before, error checks as explained below can be executed. Cases where errors are issued by the error checks are 1) a case where a workflow WF is not associated (such as a case where the flow is merely arranged and where an arrow stipulating the order of the flow is not displayed), 2) a case where necessary activities 23a are not complete in view of an activity group attribute (such as a case where any necessary activity 23a has been deleted), 3) a case where, when the order of execution is stipulated within an identical group, a workflow has been created in a wrong order, 4) a case where an activity 23a cannot operate with a device software version which has been acquired by a predetermined method of acquiring the device software version, and so forth.

4. Workflow Viewer Function

Next, the details of the workflow viewer function 32 will be described with reference to FIG. 34.

Figure 34:
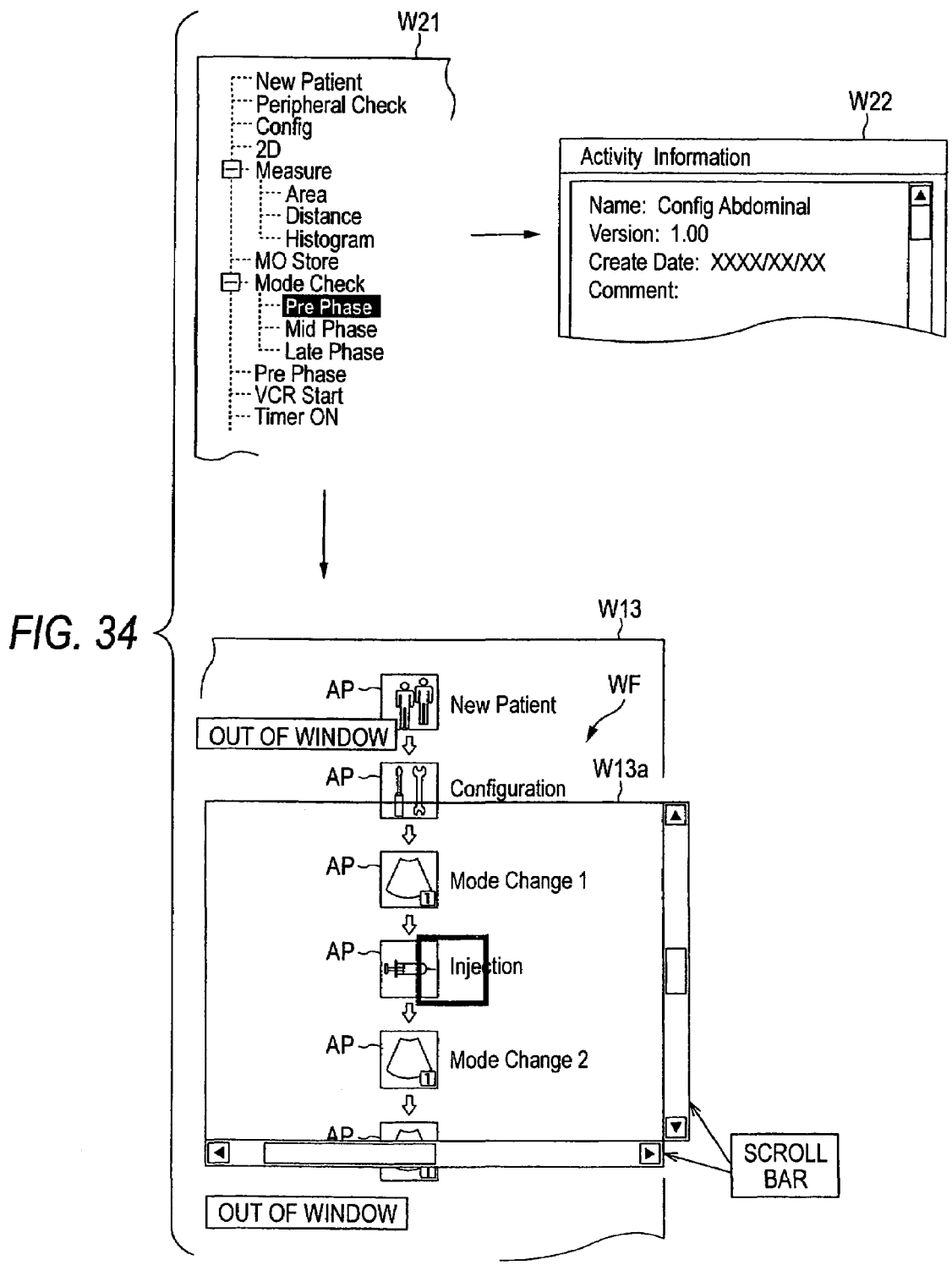
FIG. 34 is a diagram for explaining the details of a workflow viewer function.

According to the workflow viewer function 32, as shown in FIG. 34, a state where the whole hierarchy of the workflow created as stated above is expanded is first displayed on the workflow list display screen W21 within the workflow viewer screen W20.

When a pertinent activity existing at any desired hierarchical level (or its hierarchical name) is double-clicked in the hierarchical display state of the workflow by a user operation, display changeover from the workflow viewer screen W20 to the workflow edit screen W10 is automatically effected on the monitor as shown in FIG. 34. On the workflow design screen 13 within the workflow edit screen W10 after the display changeover, an activity icon AP which corresponds to the pertinent activity 23a double-clicked on the preceding workflow list display screen W21 is displayed in a selected state as shown in FIG. 34.

Besides, in a case where the double-clicked pertinent activity 23a does not exist at a hierarchical level within the main workflow, but where it exists at a hierarchical level within the lower subworkflow, the corresponding subworkflow screen W13a is displayed on the workflow design screen W13 as shown in FIG. 34, and an activity icon AP which corresponds to the double-clicked pertinent activity 23a is displayed in a selected state on the subworkflow screen W13a.

Incidentally, the pertinent activity has its display position adjusted appropriately so as to be displayed within the workflow design screen W13.

The workflow list display screen W21 can be printed in both the cases of a state where the hierarchy of the workflow is closed and a state where the hierarchy is all expanded down to lower levels. The changeover operation of the setups of the hierarchical printing is effected on a predetermined GUI screen which is displayed by the selection of the "Option" item within the "Tool" menu M5 on the menu bar BR2.

Besides, when the pertinent activity is clicked on the workflow list display screen W21 by the user operation, information items on the pertinent activity, for example, the items of "Name of Activity (having, for example, at most 32 characters)", "Version of Activity", "Software version of Ultrasonic diagnostic equipment 1 (host system) Not operating", "Build No. of Activity", "Group identification ID", "In-group execution sequence", "Plurality of keywords (each having, for example, 32 characters)", "Date and Hour of Creation", "Copyright (of 256 characters)", and "Comments (of 256 characters)" are displayed on the activity information display screen W22.

Besides, the workflow viewer function 32 includes, not only the above, but also the addition/deletion of the activity and the addition/deletion of a new activity, and also, such an edit function as checking the matchability of the activity with another activity on the basis of version check execution in the case of the addition.

5. Custom Activity Registration Function

Next, the details of the custom activity registration function 33 will be described.

According to the custom activity registration function 33, the user can create and register activities by himself/herself. The custom activities to be created here include, for example, a general-use activity (key emulation activity) which outputs the panel switch event of the host system (ultrasonic diagnostic equipment 1), and an activity (formula activity) which permits the user to define a formula peculiarly and which performs a defined computation for the input values of the activity so as to output a computed result. However, a switch code is selected from among codes previously built in. Besides, only activities each having numerical inputs or an output I/F can be connected.

Regarding the execution attributes of the custom activities, the same attributes as those of the ordinary activities stated before can be set. Besides, the user registration is performed on the page of the "User" tab TB12 within the activity library screen W12. The page of the "User" tab TB12 can be added by the selection of the "Add to User library" item within the "Workflow" menu M3 on the menu bar BR2.

6. Examination Time Simulator Function

Next, the details of the examination time simulator function 34 will be described.

According to the examination time simulator function 34, an examination time period in the case of performing an examination by actually using the workflow WF designed as stated above is estimated from the workflow WF. The estimation is made on the basis of the computation of the total time period of required time periods which are set in activities units or group units beforehand. In the case of each individual activity unit, the required time period is set by inputting an average time period which is required from the processing start to the end of an activity 23a, and in the case of each individual group unit, it is set by inputting an average time period which is required from the processing start to the end of grouped activities 23a (by inputting the average value of candidates in the existence of the plurality of subworkflow candidates). Thus, the total time period of the required time periods in activity units or group units is computed from the workflow WF and is displayed.

7. Insurance Points Computation Function

Next, the details of the insurance points computation function 35 will be described.

According to the insurance points computation function 35, insurance points in the case of performing an examination by actually using the workflow WF designed as stated above are computed from the workflow WF. The computation of the insurance points is performed by finding the total points of insurance points which are set in activity units or group units beforehand.

In the case of each individual activity unit, the insurance points are set by inputting insurance points which are required from the processing start to the end of an activity 23a, and in the case of each individual group unit, they are set by inputting insurance points which are required from the processing start to the end of grouped activities 23a (by inputting the average value of candidates in the existence of the plurality of subworkflow candidates). Thus, the total points of the insurance points in activity units or group units are computed from the workflow WF and are displayed.

8. Examination Status Monitor Function

Next, an operating example of the examination status monitor function 36 will be described.

According to the examination status monitor function 36, in a case where the ultrasonic diagnostic equipment 1 in network connection is performing the workflow system 21, the status of the performance can be monitored on the examination status monitor screen W30.

The status of the performance includes, for example, the name of the ultrasonic diagnostic equipment (host system) 1 in the network connection, the state of execution of the workflow system 21 (if an examination has been started, if an examination has been ended, which of workflows WF is being performed, what is being measured, what mode is being watched, who is being examined, or the like), and the editing state of the workflow system 21 (is anyone editing in another place, an editing history, or the like).

9. External PC Edit Function

Next, the details of the external PC edit function 37 will be described.

According to the external PC edit function 37, the visual editor 22 can be operated in both the equipment proper 11 of the ultrasonic diagnostic equipment 1 and the external PC 3 (the operation can be coped with by an OS 45 in a foreign language).

Besides, according to the external PC edit function 37, data concerning an activity or a workflow can be synchronized between the external PC 3 and the ultrasonic diagnostic equipment (host system) 1. Thus, the version of the activity 23a and an equipment software version can be checked. The synchronization is supported so as to be executable in both the cases of data via the network and data via the medium.

The data to be synchronized include the entity of the activity 23a, workflow data, workflow library information (including information registered in the workflow user library), and activity library information (including information registered in the activity user library). Besides, a folder which is utilized for the data to-be-synchronized should preferably be based on predetermined data save folder specifications.

The data synchronization is started by a user operation, and even in the course of editing the workflow, the data can be re-synchronized, that is, new synchronization can be established any time. Adopted as reference for the data synchronization is, for example, predetermined activity information specifications for the entity of the activity 23a, the update date of an XML data file for the workflow data, the update date of an information managing file (ini file) for the workflow library information, the update date of an information managing file (ini file) for the activity library information, and an update date for the history log file.

The data synchronization mode is set by utilizing, for example, a default value on a predetermined GUI screen through the selection of the "Option" item within the "Tool" menu MS on the menu bar BR2. Selected as the default value is any condition among, for example, 1) synchronization (both machines are synchronized to their newest information), 2) the contents of the external PC 3 are overwritten into the ultrasonic diagnostic equipment 1, 3) the contents of the ultrasonic diagnostic equipment 1 are overwritten into the external PC 3, and 4) the data are not synchronized. On this occasion, the synchronization between the external PC 3 and another external PC 3 is avoided to the utmost (is prohibited if possible), and the synchronization between the external PC 3 and the ultrasonic diagnostic equipment 1 is favorable.

Figure 35:
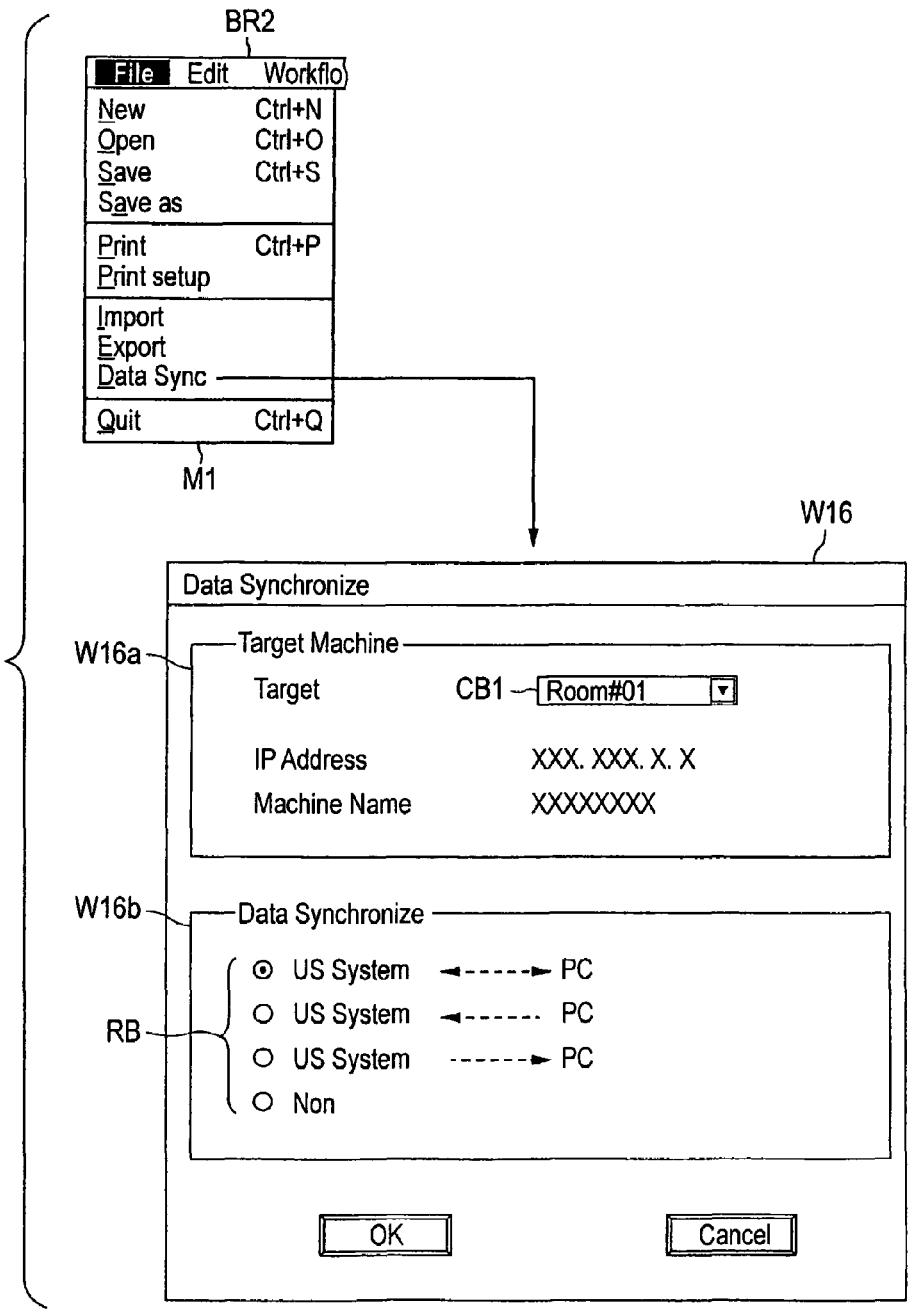
FIG. 35 is a diagram for explaining a setting example of data synchronization under a network environment.

FIG. 35 shows a setting example of the data synchronization under a network environment. The data synchronization in the network connection is set on a synchronizing dialog box W16 which is displayed by the selection of the "Data sync" item within the "File" menu M1 on the menu bar RB1.

In the dialog box W16 for the synchronization, a target machine display screen W16a and a synchronization mode setting screen W16b are displayed. A target machine (ultrasonic diagnostic equipment 1) CB1 desired for the synchronization is selected in a combo box on the target machine display screen W16a, while the synchronization mode is set with a radio button RB on the synchronization mode setting screen W16b. The synchronization mode is selected from among four sorts of conditions (refer to examples in FIG. 35) which are similar to those in the case of the above default value.

The information items of the target machine can be registered on a predetermined GUI screen which is displayed by the selection of the "Option" item of the "Tool" menu M1 on the menu bar BR2. These information items of the target machine include an IP address, a machine name (computer name), a name (of, for example, at most 20 characters) which is registered in the visual editor 22. The data synchronization is permitted, not only under the network environment, but also under a non-network environment when the removable medium is employed.

Incidentally, the workflow data created by the visual workflow editor 22 can be exported/imported to and from the hard disk in the ultrasonic diagnostic equipment 1 or another external PC 3, and the XML format is favorable as an example of the file format of the data.

10. Wizard Function

Next, the details of the wizard (help) function 40 will be described.

According to the help function 40, the help screen HW (refer to FIG. 11) stated before is activated through the selection of the "Help" menu M6 on the menu bar BR2 by a user operation, and information which the user wants to know, for example, help explanation about the operating method of the visual editor 22 is displayed on the help screen HW.

Besides, in a case where each object on the screen, such as the property of an activity icon AP or activity 23a, is focused, help explanation for the pertinent object is displayed on the help screen HW similar to the foregoing by the help function 40, in such a way that the user presses a predetermined key, for example, an "F1" function key on the keyboard 33 of the external PC 3.

Besides, in a case where the mouse cursor has overlapped any object on the screen, a chip hint is displayed by the help function 40. By way of example, in a case where the object overlapped by the mouse cursor is any menu button, its name and simple explanation are displayed as the chip hint, and in a case where the object overlapped by the mouse cursor is any activity icon AP, the name of the corresponding activity 23a is displayed.

11. Outline of General Operation

Figure 36:
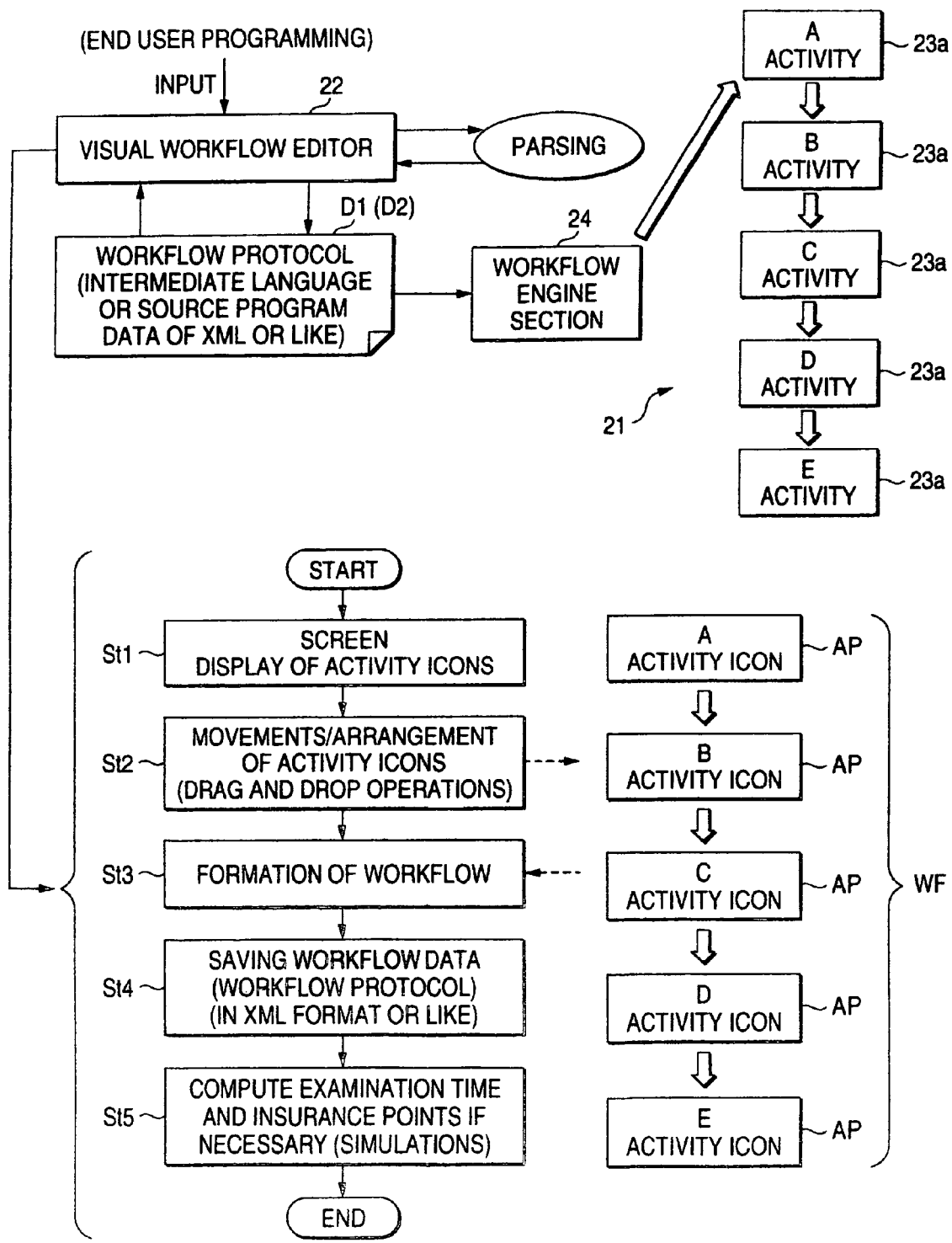
FIG. 36 is a diagram for explaining the outline of the general operation of an embodiment.

FIG. 36 is for explaining the outline of the general operation in the system configuration described above. Referring to FIG. 36, in accordance with the system configuration, the above processing is executed on the visual editor 22 by user operations (programming operations) before an examination.

More specifically, in the user operations, the screen display of activity icons AP-AP corresponding to individual activities 23a-23a (step St1), the movements/arrangement (drag & drop operations) thereof (step St2), and the formation of a workflow (step St3) are performed as in an illustrated processing flow by the processing of the visual editor 22. In the illustrated example, the workflow WF is formed in such a way that the five activity icons AP-AP A, B, C, D and E are arrayed in this order. By the way, in forming the workflow, a workflow template in the workflow library is loaded from the workflow system 21 and is referred to (reutilized) as may be needed. In case of utilizing the workflow template, the workflow WF need not be created from the very beginning, and the formation thereof can be simplified more.

Subsequently, the workflow WF is saved (if necessary, user-registered) as workflow data (workflow protocol data D1, workflow template data D2) in a predetermined data format (in an intermediate language, or source program data in the XML format or the like) (step St4), and the required examination time period and total insurance points of the workflow are computed (simulated) as may be needed (step St5).

When the workflow WF is formed by the intuitive and visual user operations, such as the drag & drop operations of the individual activity icons AP-AP, and the workflow data D1, D2 are saved as described above, the workflow data D1, D2 are stored in the workflow file section of the workflow system (refer to FIG. 2) via a predetermined check such as parsing.

Thereafter, in the examination, owing to the operation of the workflow system 21, the workflow data (workflow protocol data D1) in the workflow file section are read out by the workflow engine section 24, and the activities 23a-23a described (defined) in the workflow protocol data D1 are sequentially executed in the described order (in the illustrated example, the activities 23a-23a A, B, C, D and E are sequentially executed in this order) by the processing of the workflow engine section 24, whereby the operation of the ultrasonic diagnostic equipment 1 is controlled along the workflow WF.

In accordance with this embodiment, accordingly, the data of a workflow protocol for use in a workflow system can be easily and quickly edited and created intuitively by visual operations on a screen, whereby the advantages of the workflow system can be demonstrated to the utmost. That is, chances for the utilization of the workflow system are expanded, and even users such as beginners, who are slightly skilled in an ultrasonic diagnostic equipment and have experienced operations little, can master an operating method promptly and can operate the equipment more easily. Moreover, since the required time period and insurance points of an examination can be computed by the workflow protocol beforehand, a preceding examination plan is easily formed as one which is more based on realities.

Incidentally, the present invention is not restricted to the foregoing embodiments typically exemplified, but one skilled in the art can suggest various modifications and alterations on the basis of contents defined in the appended claims and within a scope not departing from the purport thereof, and the modifications and alterations shall fall within the scope of the right of the invention.

The invention claimed is:

1. A method of controlling an ultrasonic diagnostic equipment which projects ultrasonic signals into a patient, and which forms an ultrasonic image on the basis of reflection echoes from the patient, comprising:
   displaying a list of activities which are defined as functional units of an examination procedure of steps, and defined contents of a workflow protocol in which the plurality of activities are arrayed in a sequence of execution of the activities, on a screen by using icons;
   adding the activities within the list, to the defined contents by drag & drop operations;
   saving the resulting defined contents in a form which is executable by the ultrasonic diagnostic equipment;
   controlling equipment operations including the generation of the ultrasonic image, in accordance with the workflow protocol based on the examination procedure of steps created beforehand; and
   visually editing the workflow protocol on the screen,
   wherein the visually editing comprises:
      displaying icons on a screen, for activities which are defined as functional units of the examination procedure of steps, each of the icons including a schematic picture for representing each of the corresponding activities;
      moving the icons and arraying them in a predetermined order through user operations including drag & drop operations, thereby to form a workflow on the screen; and
      saving the workflow in a predetermined format which is executable by an ultrasonic diagnostic equipment, and
      wherein the visually editing computes the total time period which would elapse during an actual conduct of the workflow protocol being edited as a simulation.

2. A method of controlling an ultrasonic diagnostic equipment as defined in claim 1, wherein the list displays the activities in group units, and the groups are changed-over by selecting a group list part on the screen.

3. An ultrasonic diagnostic equipment which projects ultrasonic signals into a patient, and which forms an ultrasonic image on the basis of reflection echoes from the patient, comprising:
   a displaying unit configured to display a list of activities which are defined as functional units of an examination procedure of steps, and defined contents of a workflow protocol in which the plurality of activities are arrayed in a sequence of execution of the activities, on a screen by using icons;
   an adding unit configured to add the activities within the list, to the defined contents by drag & drop operations;
   a saving unit configured to save the resulting defined contents in a form which is executable by the ultrasonic diagnostic equipment;
   a controlling unit configured to control equipment operations including the generation of the ultrasonic image, in accordance with the workflow protocol based on the examination procedure of steps created beforehand; and
   an editing unit configured to visually edit the workflow protocol on the screen,
   wherein the editing unit comprises:
      a first unit configured to display icons on a screen, for activities which are defined as functional units of the examination procedure of steps, each of the icons including a schematic picture for representing each of the corresponding activities;
      a second unit configured to move the icons and array them in a predetermined order through user operations including drag & drop operations, thereby to form a workflow on the screen; and
      a third unit configured to save the workflow in a predetermined format which is executable by the ultrasonic diagnostic equipment, and
      wherein the editing unit is configured to compute the total time period which would elapse during an actual conduct of the workflow protocol being edited as a simulation.

4. An ultrasonic diagnostic equipment as defined in claim 3, wherein the list displays the activities in group units, and the groups are changed-over by selecting a group list part on the screen.

\* \* \* \* \*